US011045506B2

(12) United States Patent
Pamer et al.

(10) Patent No.: US 11,045,506 B2
(45) Date of Patent: Jun. 29, 2021

(54) METHODS AND COMPOSITIONS FOR IDENTIFYING AND TREATING SUBJECTS AT RISK FOR CHECKPOINT BLOCKADE THERAPY ASSOCIATED COLITIS

(71) Applicant: Memorial Sloan-Kettering Cancer Center, New York, NY (US)

(72) Inventors: Eric Pamer, Montclair, NJ (US); Jedd D. Wolchok, New York, NY (US); Krista Dubin, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 15/984,613

(22) Filed: May 21, 2018

(65) Prior Publication Data

US 2018/0360892 A1 Dec. 20, 2018

Related U.S. Application Data

(63) Continuation of application No. PCT/US2016/063530, filed on Nov. 23, 2016.

(60) Provisional application No. 62/259,445, filed on Nov. 24, 2015.

(51) Int. Cl.
| | |
|---|---|
| *A01N 63/00* | (2020.01) |
| *A61K 35/742* | (2015.01) |
| *A61K 45/06* | (2006.01) |
| *G01N 33/569* | (2006.01) |
| *A23L 5/00* | (2016.01) |
| *A61P 1/00* | (2006.01) |
| *A61K 9/00* | (2006.01) |
| *A61K 35/00* | (2006.01) |

(52) U.S. Cl.
CPC .............. *A61K 35/742* (2013.01); *A23L 5/00* (2016.08); *A61K 9/0031* (2013.01); *A61K 9/0043* (2013.01); *A61K 9/0053* (2013.01); *A61K 45/06* (2013.01); *A61P 1/00* (2018.01); *G01N 33/56911* (2013.01); *A61K 2035/115* (2013.01); *G01N 2800/067* (2013.01)

(58) Field of Classification Search
CPC .................................................. A61K 35/742
See application file for complete search history.

(56) References Cited

U.S. PATENT DOCUMENTS

| | | | |
|---|---|---|---|
| 2009/0169582 A1* | 7/2009 | Chua ............... | C07K 14/43531 424/200.1 |
| 2014/0044677 A1* | 2/2014 | Qvit-Raz ............ | C12N 15/746 424/93.2 |
| 2015/0238544 A1 | 8/2015 | Jones et al. | |

FOREIGN PATENT DOCUMENTS

| | | |
|---|---|---|
| WO | WO 2013/175038 A1 | 11/2013 |
| WO | WO 2014/082050 A1 | 5/2014 |
| WO | WO 2015/166492 A2 | 11/2015 |

OTHER PUBLICATIONS

Cline, "Perspectives for Gene Therapy: Inserting New Genetic Information into Mammalian Cells by Physical Techniques and Viral Vectors," Pharmac. Ther. 29:69-92 (1985).
Cotten et al., "Receptor-Mediated Transport of DNA into Eukaryotic Cells," Meth. Enzymol. 217:618-644 (1993).
Goldspiel et al., "Human Gene Therapy," Clinical Pharmacy 12:488-505 (1993).
International Search Report dated Mar. 10, 2017 in International Application No. PCT/US2016/063530.
Kriegler, Gene Transfer and Expression, A Laboratory Manual, Stockton Press, NY (1990).
Kron et al., "Adenovirus Vectors and Subviral Particles for Protein and Peptide Delivery," Curr Gene Ther 12:362-373 (2012).
Loeffler et al., "Gene Transfer into Primary and Established Mammalian Cell Lines with Lipopolyamine-Coated DNA," Meth. Enzymol. 217:599-618 (1993).
Magnusdottir et al., "Systematic genome assessment of B-vitamin biosynthesis suggests co-operation among gut microbes," Frontiers in Genetics, 6(148):1-18 (2015).
Morgan et al., "Human Gene Therapy," Ann. Rev. Biochem. 62:191-217 (1993).
Mulligan, "The Basic Science of Gene Therapy," Science 260(5110):926-932 (1993).
Tibtech 11:155-215 (May 1993), (Robinson et al)
Tolstoshev, "Gene Therapy, Concepts, Current Trials and Future Directions," Ann. Rev. Pharmacol. Toxicol. 32:573-596 (1993).
Vetizou et al., "Anticancer immunotherapy by CTLA-4 blockade relies on the gut microbiota," Science 350(6264):1079-1084 (2015).
Wu et al., "Delivery systems for gene therapy," Biotherapy 3:87-95 (1991).
Yi et al., "Current Advances in Retroviral Gene Therapy," Curr Gene Ther 11:218-228 (2011).
Cano et al., "*Bacteroides uniformis* CECT 7771 Ameliorates Metabolic and Immunological Dysfunction in Mice with High-Fat-Diet Induced Obesity," PLoS One 7(7):e41079 (2012).

(Continued)

*Primary Examiner* — Albert M Navarro
(74) *Attorney, Agent, or Firm* — Baker Botts L.L.P.

(57) ABSTRACT

The present invention relates to methods and compositions for identifying subjects treated with or considered for treatment with checkpoint blockade therapeutic agents that are at higher or lower risk for developing checkpoint therapy associated colitis, by analyzing the intestinal microbiome of those subjects. It is based, at least in part, on the discovery that the abundance of certain intestinal microbiota of the phyla Bacteroidetes, including the bacteria in the families Bacteroidaceae, Rikenellaceae, and Barnesillaceae, and/or an increase or decrease in microbial genetic pathways involved in polyamine transport and/or B vitamin biosynthesis (e.g., (riboflavin (B2), pantothenate (B5) and thiamine (B1)) are associated with the likelihood of developing checkpoint therapy associated colitis.

Figure 1A:
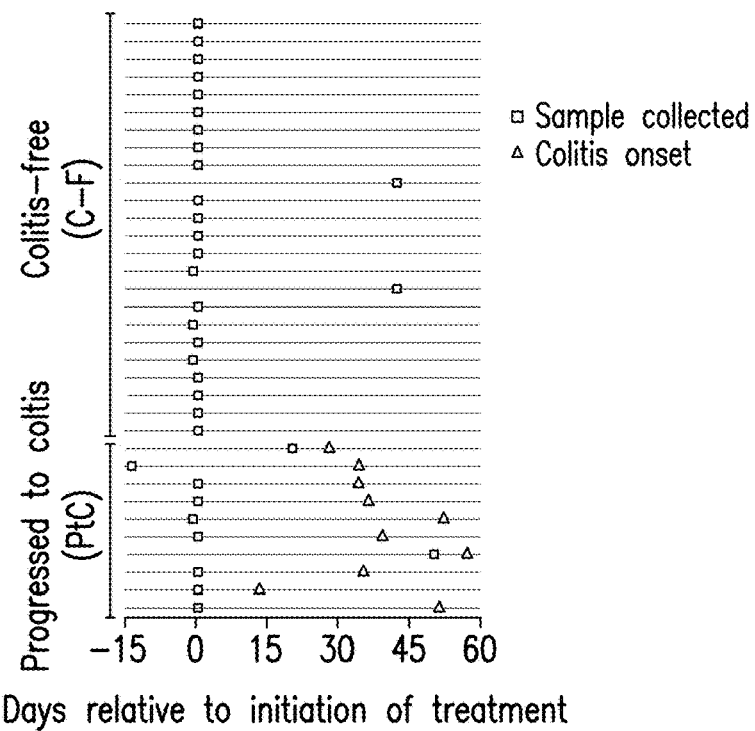

6 Claims, 23 Drawing Sheets
Specification includes a Sequence Listing.

(56) References Cited

OTHER PUBLICATIONS

Dubin et al., "Intestinal microbiome analyses identify melanoma patients at risk for checkpoint-blockade-induced colitis," Nature Communications 7(1):1-8 (2016).
Gupta et al., "Systematic review: colitis associated with anti-CTLA-4 therapy," Alimentary Pharmacology & Therapeutics 42:406-417 (2015).
Sugita et al., "The vitamin B-12-producing ability of the intestinal microflora of freshwater fish," Aquaculture 92:267-276 (1991).
Supplementary European Search Report dated May 17, 2019 in Application No. EP 16869244.

\* cited by examiner

METHODS AND COMPOSITIONS FOR IDENTIFYING AND TREATING SUBJECTS AT RISK FOR CHECKPOINT BLOCKADE THERAPY ASSOCIATED COLITIS

CROSS-REFERENCE TO RELATED APPLICATIONS

This application is a continuation application of International application PCT/US2016/063530 filed Nov. 23, 2016; which claims priority to U.S. Provisional Application Ser. No. 62/259,445, filed on Nov. 24, 2015, priority to which is claimed, and the contents of which are incorporated by reference in their entirety herein.

STATEMENT OF GOVERNMENT INTEREST

This invention was made with government support under AI042135 and CA008748 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Dec. 20, 2016, is named 072734_0437_SL.txt and is 1,090 bytes in size.

1. INTRODUCTION

The present invention relates to compositions and methods for identifying subjects treated with checkpoint blockade agents that are at higher or lower risk for developing checkpoint blockade therapy associated colitis, by analyzing the intestinal microbiome of those subjects, and related therapeutic compositions and methods to reduce the risk of checkpoint blockade therapy associated colitis.

2. BACKGROUND OF THE INVENTION

The intestine of mammals is densely colonized by hundreds of microbial species that coexist symbiotically with their hosts. The microbes, collectively referred to as the intestinal microbiota, form the intestinal microbiome and contribute to numerous aspects of host health, including nutrient metabolism, homeostasis of intestinal tissues, development of innate and adaptive immune responses, and more generally, defense against intestinal infection. Healthy individuals harbor distinct microbial populations in their intestinal tract that vary markedly in composition. Identifying the microbial species that promote homeostasis or other healthy benefits and those that drive inflammation or have other unhelpful or harmful effects has remained difficult to do in the clinical context, particularly with chronic inflammatory conditions such as Inflammatory Bowel Disease (IBD). Certain bacteria preferentially expand following inflammation, which alters the intestinal microbiota's composition. Thus, as most patients seek medical attention after inflammation has developed, it is difficult to define the microbiota composition of the intestinal microbiome that precedes the development of colitis.

Ipilimumab, a monoclonal antibody that blocks the co-inhibitory molecule CTLA-4, is an immunomodulatory therapy that acts by checkpoint inhibition/blockade and provides effective treatment against metastatic melanoma. Inhibition of CTLA-4 signaling dampens negative regulation of T cells, thereby enhancing anti-tumor responses because T cells modulate immune responses in the body. Early in treatment, many Ipilimumab recipients develop intestinal inflammation as a result of mucosal immune dysregulation. It is beneficial to identify those subjects at higher risk, relative to the other Ipilimumab recipients, of developing intestinal inflammation and associated colitis.

3. SUMMARY OF THE INVENTION

The present invention relates to methods and compositions for analyzing the intestinal microbiome of subjects treated, or intended to be treated, with checkpoint blockade therapeutic agents in order to identify subjects at higher or lower risk for developing checkpoint blockade therapy associated colitis. It is based, at least in part, on the results of experiments utilizing next-generation metagenomic sequencing to identify biomarkers associated with resistance to new-onset, immune-mediated colitis in the context of checkpoint blockade therapy, including the discoveries that increased fecal abundance of the Bacteroidetes phylum and three of its families (Bacteroidaceae, Rikenellaceae, and Barnesiellaceae) as well as microbial genetic pathways involving polyamine transport and B vitamin biosynthesis (e.g., riboflavin (B2), pantothenate (B5) and thiamine (B1)) positively correlated with resistance to the development of colitis following checkpoint blockade therapy.

According to one non-limiting embodiment, the invention provides a pharmaceutical composition including one or more isolated bacteria or spores thereof, wherein the isolated bacteria or spores thereof are a member of the Bacteriodetes, and further including a biocompatible pharmaceutical carrier. The isolated bacteria or spores thereof may be a member of the Bacterioidaceae family, a member of the Rikenellaceae family, and/or a member of the Barnesiellaceae family.

According to another non-limiting embodiment, the invention provides a pharmaceutical composition including one or more isolated bacteria or spores thereof, wherein the isolated bacteria or spores thereof includes at least one bacterial genetic module for polyamine transport or B vitamin biosynthesis, and further including a biocompatible pharmaceutical carrier. The at least one bacterial genetic module for B vitamin biosynthesis may be for riboflavin biosynthesis, for pantothenate biosynthesis, and/or for thiamine biosynthesis. The isolated bacteria or spores thereof may include at least two, at least three, or at least four bacterial genetic modules for polyamine transport or B vitamin biosynthesis.

In other non limiting embodiments, any of the above compositions may have the following additional features, which may be combined with one another and with other aspects of the specification unless clearly mutually exclusive. The isolated bacteria may be a recombinant cell. The isolated bacteria or spores thereof may be present in a cluster. The composition may be formulated for oral, nasogastric, or rectal administration. The composition may be a liquid, suspension, dried powder, tablet, capsule or food product. The composition may further include a probiotic bacteria, probiotic yeast, or a combination thereof; a prebiotic; a postbiotic; an antibiotic; or combination thereof. The one or more isolated bacteria or spores thereof may be present in an amount that can reduce the risk or severity of checkpoint blockade therapy associated colitis in a subject administered the composition.

In other non-limiting embodiments, the present invention provides a method of treating checkpoint blockade associated colitis in a subject by administering to the subject a therapeutically effective amount of any of the above compositions.

In other non-limiting embodiments, the present invention provides the use of any of the above compositions for the treatment of checkpoint blockade associated colitis in a subject. The use may include administering to the subject a therapeutically effective amount of the composition.

In another non-limiting embodiment, the present invention provides a method of identifying subjects at higher or lower risk of developing checkpoint blockade therapy associated colitis or likely to experience more or less severe checkpoint blockade therapy associated colitis. The method includes determining the level of one or more bacteria or spores thereof of the Bacteriodetes phylum or one or more bacteria or spores thereof including at least one bacterial genetic module for polyamine transport or B vitamin biosynthesis in the intestinal microbiome of a subject and comparing the level of the one or more bacteria or spores therein with at least one reference bacteria level. The method further includes diagnosing the subject as having a higher risk of developing checkpoint blockade therapy associated colitis or likely to experience more severe checkpoint blockade therapy associated colitis if the level of one or more bacteria or spores thereof is lower than at least one reference bacteria level, or diagnosing the subject as having a lower risk of developing checkpoint blockade therapy associated colitis or likely to experience less severe checkpoint blockade therapy associated colitis if the level of one or more bacteria or spores thereof is greater than at least one reference bacteria level. The one or more bacteria or spores thereof in the Bacteriodetes phylum may include one or more bacteria or spores thereof in the Bacteroidaceae family, in the Rikenellaceae family, and/or in the Barnesiellaceae family. The at least one bacterial genetic module for B vitamin biosynthesis may include a bacterial genetic module for riboflavin biosynthesis, for pantothenate biosynthesis, and/or for thiamine biosynthesis.

In other non limiting embodiments, any of the above methods may have the following additional features, which may be combined with one another and with other aspects of the specification unless clearly mutually exclusive. Determining the level of one or more bacteria or spores thereof of the Bacteriodetes phylum or one or more bacteria or spores thereof including at least one bacterial genetic module for polyamine transport or B vitamin biosynthesis in the intestinal microbiome of a subject may include determining in a fecal sample of the subject. Determining the level of one or more bacteria or spores thereof of the Bacteriodetes phylum or one or more bacteria or spores thereof including at least one bacterial genetic module for polyamine transport or B vitamin biosynthesis in the intestinal microbiome of a subject may include conducting metagenomic sequencing to identify biomarkers associated with the bacteria or spores thereof. The reference bacteria level may be based on relative abundance of the bacteria or spores thereof as compared to other bacteria in the intestinal microbiome. The method may include determining the level of two or more bacteria or spores thereof of the Bacteriodetes phylum or one or more bacteria or spores thereof including at least one bacterial genetic module for polyamine transport or B vitamin biosynthesis in the intestinal microbiome of a subject and comparing the levels to two reference bacterial levels for the respective bacteria or spores.

In another non-limiting embodiment, the invention provides a method of identifying subjects at higher or lower risk of developing checkpoint blockade therapy associated colitis or likely to experience more or less severe checkpoint blockade therapy associated colitis. The method includes determining the level of at least one bacterial genetic module for polyamine transport or B vitamin biosynthesis in the intestinal microbiome of a subject and comparing the level of the at least one bacterial genetic module with at least one reference genetic module level. The method further includes diagnosing the subject as having a higher risk of developing checkpoint blockade therapy associated colitis or likely to experience more severe checkpoint blockade therapy associated colitis if the bacterial genetic module level is lower than at least one reference bacterial genetic module level or diagnosing the subject as having a lower risk of developing checkpoint blockade therapy associated colitis or likely to experience less severe checkpoint blockade therapy associated colitis if the bacterial genetic module level is greater than at least one reference bacterial genetic module level. The at least one bacterial genetic module for B vitamin biosynthesis may include a bacterial genetic module for riboflavin biosynthesis, for pantothenate biosynthesis and/or for thiamine biosynthesis. Determining the level of at least two, three, or four bacterial genetic modules for polyamine transport or B vitamin biosynthesis in the intestinal microbiome of a subject and comparing the levels to two, three, or four reference bacterial genetic module levels for the respective bacterial genetic modules.

According to another non-limiting embodiment, the invention provides a method of treating a subject with or at risk of developing checkpoint blockade therapy associated colitis by diagnosing the subject as having a higher risk of developing checkpoint blockade therapy associated colitis or likely to experience more severe checkpoint blockade therapy using any of the above methods and administering to the subject any of the above compositions.

In other non limiting embodiments, any of the above methods may have the following additional features, which may be combined with one another and with other aspects of the specification unless clearly mutually exclusive. The checkpoint blockade therapy may include a therapy selected from the group consisting of anti-CTLA4 antibodies, anti-PD-1 antibodies, and anti-PD-L1 antibodies, and fragments thereof, single chain antibodies, and fusion proteins including antibody fragments, a CpG-oligonucleotide immunotherapeutic agent and cyclophosphamide, and any combinations thereof. The subject may suffer from cancer and the subject may be concurrently or sequentially administered an additional agent with anti-cancer activity. The subject may suffer from an infectious disease and the subject may be concurrently or sequentially administered an additional agent with anti-infection activity.

According to another non-limiting embodiment, the invention provides a kit for of identifying subjects at higher or lower risk of developing checkpoint blockade therapy associated colitis or likely to experience more or less severe checkpoint blockade therapy associated colitis, the kit including means for detecting the level of one or more bacteria or spores thereof of the Bacteriodetes phylum or one or more bacteria or spores thereof including at least one bacterial genetic module for polyamine transport or B vitamin biosynthesis in the intestinal microbiome of a subject or means for detecting the level of at least one bacterial genetic module for polyamine transport or B vitamin biosynthesis in the intestinal microbiome of a subject.

In other non limiting embodiments, any of the above methods may have the following additional features, which may be combined with one another and with other aspects of the specification unless clearly mutually exclusive. The kits may be used to implement any of the above methods or diagnosing steps described above, as appropriate. The means for detecting may include at least one nucleic acid primer, at least one nucleic acid probe, at least one antibody, or any combinations thereof. The kit may include any composition described above, which may be administer in any administering step described above.

The example section and figures below should be considered to illustrate but not limit the scope of the invention. Although certain embodiments are discussed throughout this application, elements from different embodiments are suitable for combination with one another, even when such combination is not expressly discussed, unless such combination is clearly not functional or possible.

4. BRIEF DESCRIPTION OF THE FIGURES

FIG. 1 shows differences in microbial populations in patients receiving checkpoint blockade therapy who progress to colitis and those who are colitis free. FIG. 1A is a graph of colitis status (Colitis-Free (C-F) or Progressed-to-Colitis (PtC)) versus days post-initiation of treatment with ipilimumab. FIG. 1B is a Venn diagram of operational taxonomic units (OTUs) in Colitis-Free (C-F) or Progressed-to-Colitis (PtC) patients and shared OTUs. FIG. 1C is a graph of mean relative OTU abundance in Colitis-Free (C-F) versus Progressed-to-Colitis (PtC) patients and shared OTUs. FIG. 1D is a graph of total OTU abundance in Colitis-Free (C-F) or Progressed-to-Colitis (PtC) patients and shared OTUs. FIG. 1E is a graph of the frequency of OTUs in Colitis-Free (C-F) or Progressed-to-Colitis (PtC) and frequency of shared OTUs.

FIG. 2 shows the intestinal microbiota diversity in patients receiving checkpoint blockade therapy who Colitis-Free (C-F) and those who were Colitis-Free (C-F). Height of bar represents the mean, error bars represent standard deviation. n.s., not significant. FIG. 2A is a graph of intestinal microbiota diversity as determined by the Inverse Simplson index. FIG. 2B is a graph of intestinal microbiota diversity as determined by the Shannon estimator. FIG. 2C is a graph of intestinal microbiota diversity as determined by the Chao estimator. FIG. 2D is a graph of intestinal microbiota diversity as determined by rarefaction curves. Data for patients who Progressed-to-Colitis is shown in the upper graph. Data for patients who remained Colitis-Free is shown in the lower graph.

Figure 3A:
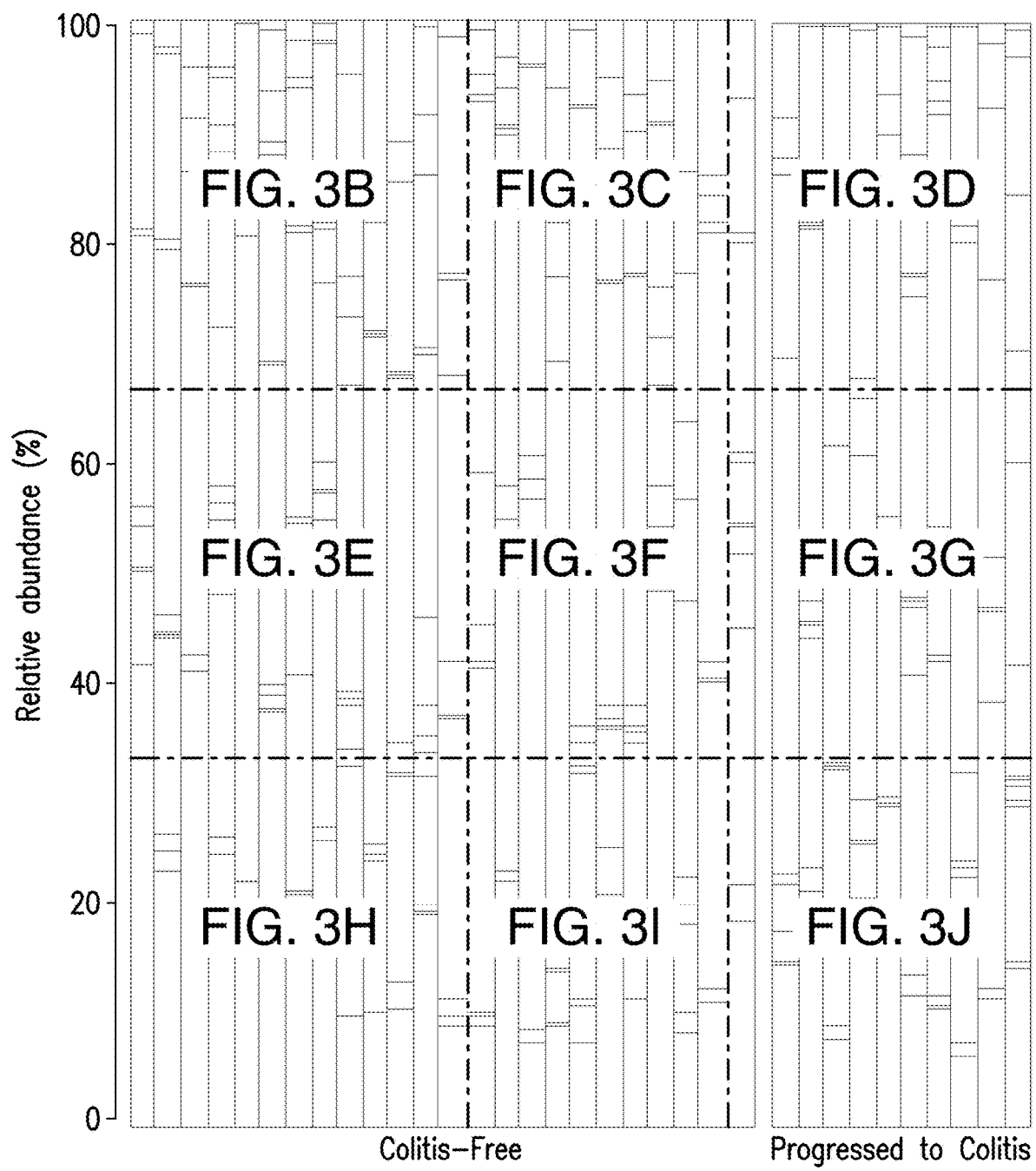

FIG. 3 shows the composition of intestinal microbiota in patients treated receiving checkpoint blockade therapy who progressed to colitis and those who are colitis-free FIGS. 3A-3J is a plot of the relative abundance of various microbes at a family taxonomic level in Colitis-Free and Progressed-to-Colitis patients. Families with an average abundance of 2.5% or maximum abundance of 5% are plotted. Each bar represents the fecal microbial composition of one patient. FIG. 3A is marked to show an outline of the complete plot and the locations of regions of the plot reproduced in FIGS. 3B-3J. FIG. 3K is a plot of the relative abundance of various microbes at a phylum taxonomic level in Colitis-free and Progressed-to-Colitis patients. Actino designates Actinobacteria; Bact deisgnates Bacteroidetes; Firm designates Firmicutes; Proteo designates Proteobacteria; Verr designates verrucomicrobia.

Figure 4A:
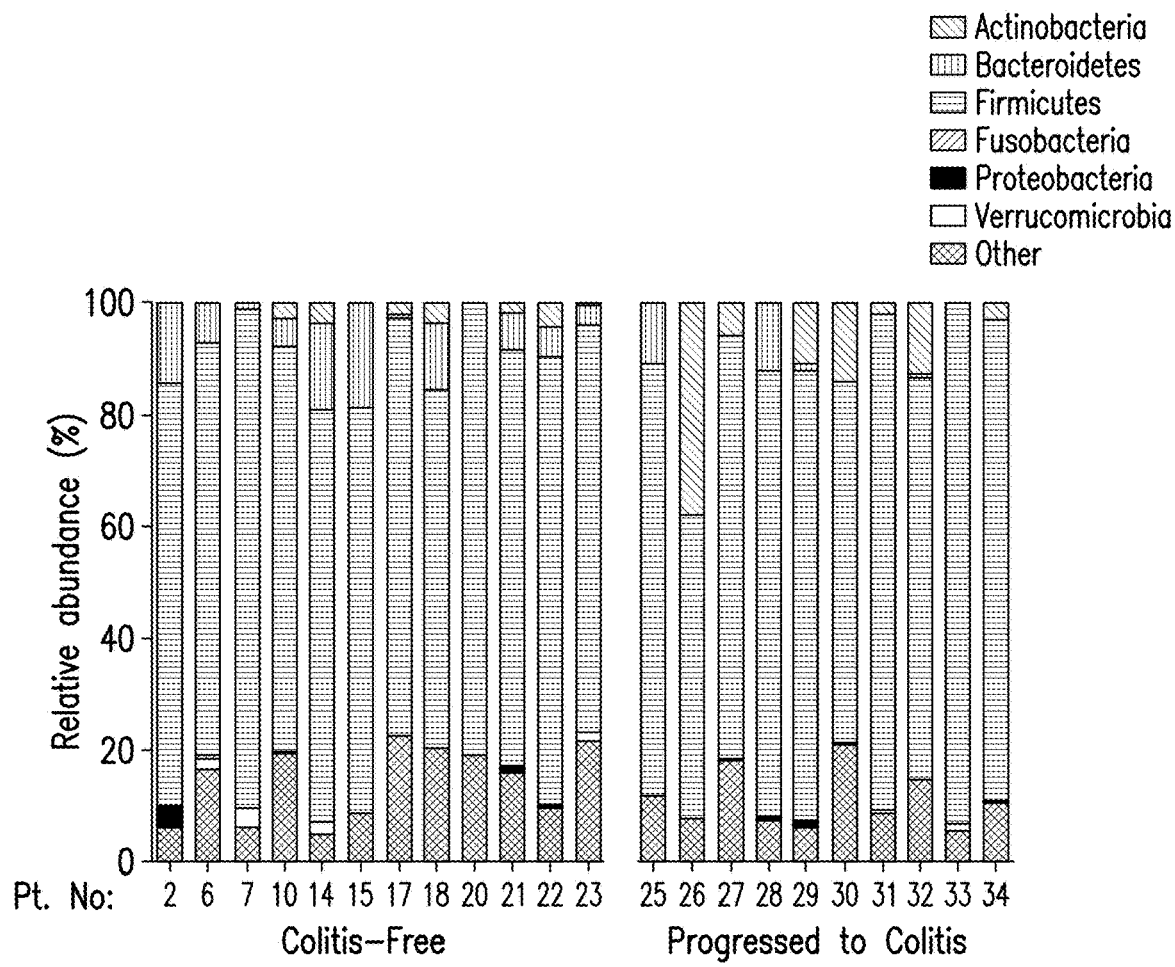
Figure 4B:
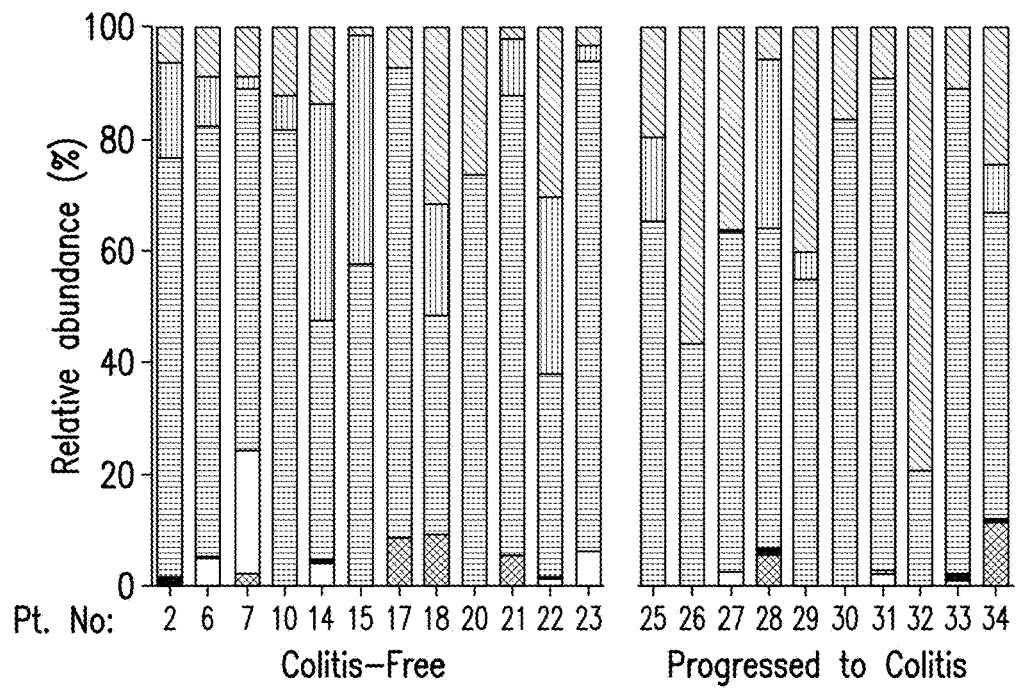

FIG. 4 shows the accuracy of bacterial taxonimic classification in patients receiving checkpoint blockade therapy who Progressed-to-Colitis or were Colitis-Free. FIG. 4A is a graph of taxonomic classifications by phylum in patients based on 16s sequencing reads. FIG. 4B is a graph of taxonimic relative abundances by phylum based on shotgun metagenomic sequencing reads calculated using MetaPhlAn.

FIG. 5 shows the relationship between abundance of intestinal microbes from the Bacteroidetes phylum and certain taxonomic families and protection from colitis in patients receiving checkpoint blockade therapy. FIG. 5A is a graph of the Spearman correlation of OTUs in Colitis-Free (C-F) patients. Taxa with p-values<0.05 are plotted. FIG. 5B is a graph of the relative abundance of phylum Bacteriodetes in Colitis-Free (C-F) or Progressed-to-Colitis (PtC) patients. For FIGS. 5C-5F, P-values were determined by Mann-Whitney test. Height of bar represents the mean, error bars represent standard deviation. r, Rho coefficient; p, p-value. FIG. 5C is a graph of the number of Bacteroidetes OTUs in Colitis-Free (C-F) or Progressed-to-Colitis (PtC) patients. FIG. 5D is a graph of the relative abundance of Bacteroidacae in Colitis-Free (C-F) or Progressed-to-Colitis (PtC) patients and a graph of respective colitis scores. FIG. 5E is a graph of the relative abundance of Rikenellaceae in Colitis-Free (C-F) or Progressed-to-Colitis (PtC) patients and a graph of respective colitis scores. FIG. 5F is a graph of the relative abundance of Barnesiellaceae in Colitis-Free (C-F) or Progressed-to-Colitis (PtC) patients and a graph of respective colitis scores.

Figure 6:
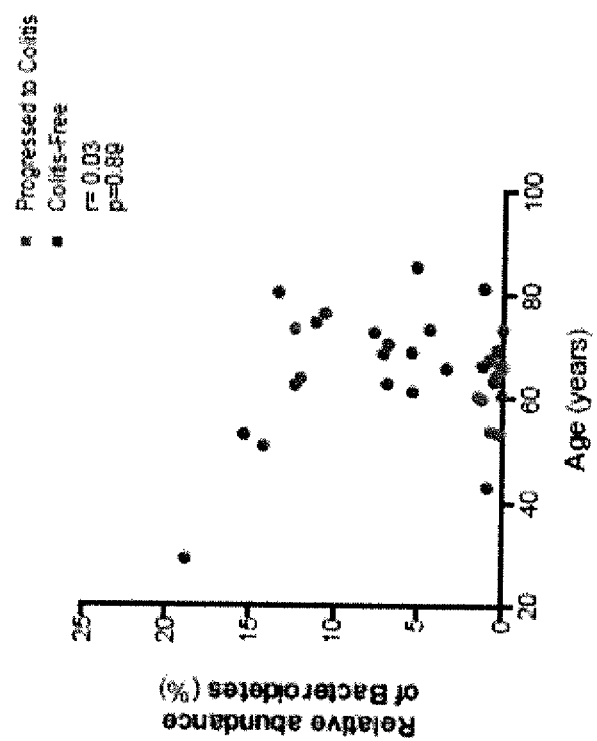

FIG. 6 is a graph of relative abundance of Bacteroidetes in patients receiving checkpoint blockade therapy versus patient age. OTUs with an average abundance greater than 0.01% within either patient group were grouped by phylum. r, Rho coefficient; p, p-value.

FIG. 7 shows the relationship between bacterial molecules involved in polyamine transport and vitamin B synthesis and resistance to colitis in patients receiving checkpoint blockage therapy. FIG. 7A is a graph of the relative abundance of Kyoto Encyclopedia of Genes and Genomes (KEGG) molecules in colitis-free or progressed to colitis patients. FIG. 7B is a graph of linear discriminant analysis effect size (LEfSe) analysis for various genetic modules in Colitis-Free (C-F) or Progressed-to-Colitis (PtC) patients. Modules with LDA score>3 are plotted. FIG. 7C is a graph of the Spearman correlation of various genetic modules in Colitis-Free (C-F) or Progressed-to-Colitis (PtC) patients. Modules with p-values<0.05 are plotted. FIG. 7D is a graph of the relative abundance of various genetic modules in Colitis-Free (C-F) or Progressed-to-Colitis (PtC) patients. Height of bar represents mean, error bars represent standard deviation. P-values were determined by Mann-Whitney test.

FIG. 8 shows the predictive accuracy of bacterial genetic modules in identifying checkpoint blockade therapy patients who progress to colitis. FIG. 8A is a graph of results of a recursive partitioning algorithm applied to Colitis-Free (C-F) or Progressed-to-Colitis (PtC) patients. FIG. 8B presents two graphs of results of predicted probability of colitis per patient (designated by patient number on the x axis) for Colitis-Free (C-F) or Progressed-to-Colitis (PtC) patients. One patient is represented per column. Specificity and sensitivity calculated based on a probability threshold of 50%. FIG. 8C is a graph of the sensitivity and specificity of various genetic modules in predicting patients' colitis status. Poly, polyamine transport system; Thi, thiamine biosynthesis; Ribo, riboflavin biosynthesis; Panto, pantothenate biosynthesis. FIG. 8D is a graph of the true positive rate versus false positive rate, referred to as the Receiver Operating Characteristic (ROC) curve, for a predictive analysis using four genetic modules in colitis-free (solid line) or progressed to colitis (dashed line) patients.

Figure 9:
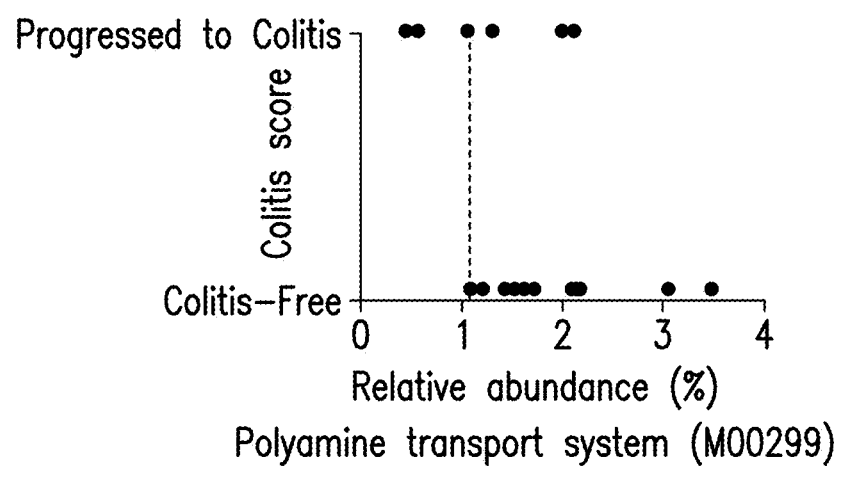

FIG. 9 is a graph of colitis score versus relative abundance of polyamine transport system in patients receiving checkpoint blockade therapy.

5. DETAILED DESCRIPTION OF THE INVENTION

The present invention relates to methods and compositions for identifying subjects treated with checkpoint blockade therapeutic agents who are at higher or lower risk for developing checkpoint blockade therapy associated colitis, by analyzing the intestinal microbiome of those subjects, and related therapeutic methods and compositions to reduce the risk of checkpoint blockade therapy associated colitis. This disclosure also relates to identification of biomarkers that predict the risk of developing colitis, which may help identify patients who are particularly susceptible to certain forms of immunotherapy-induced inflammation, such as with CTLA-4 blockade, and may facilitate preemptive treatments.

The invention is based in part on the discovery that certain intestinal microbial modules, for instance including microbiota of the Bacteroidetes phyllum, are predictive of checkpoint, particularly CTLA-4, blockade associated colitis development and correlate with protection against checkpoint, particularly CTLA-4, blockade associated colitis. The discovery is based on experiments, including those in the Examples herein, in which the intestinal microbiota of patients were characterized prior to the development of colitis and several parameters of such intestinal microbiota were assessed.

It was discovered that microbiota of the Bacteroidetes phylum are enriched in colitis-resistant patients. Members of the Bacteroidetes phylum can limit inflammation by stimulating T-regulatory cell differentiation. Further, the presence of microbiota-associated genetic modules for the bacterial polyamine transport system can accurately identify a patient's risk of developing colitis following checkpoint blockade therapy, such as CTLA-4 blockade. Polyamines, which are small cationic amines that can be exported from bacteria cells, play an anti-inflammatory role by promoting colonic epithelial cell (CEC) proliferation to maintain the epithelial barrier. The presence of microbiota-associated genetic modules for the biosynthesis of thiamine, riboflavin and pantothenate can also accurately identify a patient's risk of developing colitis following checkpoint blockade therapy, such as CTLA-4 blockade.

For clarity of description, and not by way of limitation, this section is divided into the following subsections:
(i) Methods of determining colitis risk;
(ii) Therapeutic bacteria;
(iii) Recombinant cells;
(iv) Pharmaceutical compositions;
(v) Methods of treatment; and
(vi) Kits.

The following are terms relevant to the present invention:

An "individual" or "subject" or "patient" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

In certain non-limiting embodiments, the subject suffers from a cancer or from an infectious disease, or both. In certain non-limiting embodiments, the subject is receiving or may receive checkpoint blockade therapy. In certain non-limiting embodiment, the subject is concurrently or sequentially treated with an agent in addition to the checkpoint blockade therapeutic agent, which additional agent has anti-cancer or anti-infection activity.

"Checkpoint blockade therapy" is inhibition of a protein or process that negatively regulates T cells by administering to a patient receiving the therapy a "checkpoint blockade therapeutic agent," such as a CTLA-4 inhibitor, a PD-1 inhibitor, a PD-L1 inhibitor, including anti-CTLA4 antibodies, anti-PD-1 antibodies, and anti-PD-L1 antibodies (including fragments thereof, single chain antibodies, fusion proteins, etc.), including but not limited to ipilimumab, nivolumab and pembrolizumab, or a CpG-oligonucleotide immunotherapeutic agent and cyclophosphamide.

"Colitis" is a disorder characterized by inflammation of the colon. Colitis may be assessed using the Common Terminology Criteria for Adverse Events (CTCAE), Version 4, as of Nov. 25, 2015, which defines Grade 1 colitis as asymptomatic with clinical or diagnostic observations only, Grade 2 colitis as evidenced by abdominal pain and mucus or blood in stool, Grade 3 colitis as evidenced by severe abdominal pain, a change in bowel habits, and peritoneal signs, Grade 4 colitis as evidenced by life-threatening consequences; and Grade 5 colitis as evidenced by death.

"Checkpoint blockade therapy associated colitis" is colitis that is medically indicated to be at least partially caused by checkpoint blockade therapy. Checkpoint blockade therapy associated colitis" may include colitis that first occurs in a patient receiving checkpoint blockade therapy or who has received checkpoint blockade therapy in the month prior to onset of colitis.

An "effective amount" of a substance as that term is used herein is that amount sufficient to effect beneficial or desired results, including clinical results, and, as such, an "effective amount" depends upon the context in which it is being applied. In the context of administering a composition to reduce the risk of colitis and/or administering a composition to reduce at least one sign or symptom of colitis, an effective amount of a composition described herein is an amount sufficient to prevent the onset of colitis, prevent progression of colitis to the next grade, treat and/or ameliorate colitis, regress the grade of colitis, and/or reduce the likelihood of onset or grade progression of colitis, or increase the likelihood of grade regression by at 10%, 20%, 30%, 40%, 50%, 60%, 70%, 80%, 90%, 95%, 98% or 99%.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more signs or symptoms, diminishment of extent of disease, stabilized (i.e., not worsening) state of disease, prevention of disease, delay or slowing of disease progression, remission of the disease (e.g., colitis) and/or amelioration or palliation of the disease state. The decrease can be at least a 10%, 20%, 30%, 40%, 50%, 60%, 70%, 80%, 90%, 95%, 98% or 99% decrease in severity of complications, signs or symptoms or in likelihood of progression to another grade. Treatment" can also refer to decreasing the likelihood of colitis onset or progression to a higher grade by at least 10%, 20%, 30%, 40%, 50%, 60%, 70%, 80%, 90%, 95%, 98% or 99%.

The term "expression vector" is used to denote a nucleic acid molecule that is either linear or circular, into which another nucleic acid sequence fragment of appropriate size can be integrated. Such nucleic acid fragment(s) can include additional segments that provide for transcription of a gene encoded by the nucleic acid sequence fragment. The additional segments can include and are not limited to: promoters, transcription terminators, enhancers, internal ribosome entry sites, untranslated regions, polyadenylation signals, selectable markers, origins of replication and such, as known in the art. Expression vectors are often derived from plasmids, cosmids, and viral vectors; vectors are often recombinant molecules containing nucleic acid sequences from several sources.

The term "operably linked," when applied to nucleic acid sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal.

A "nucleic acid molecule" is a single or double stranded covalently-linked sequence of nucleotides in which the 3' and 5' ends on each nucleotide are joined by phosphodiester bonds. The polynucleotide can be made up of deoxyribonucleotide bases or ribonucleotide bases. Polynucleotides include DNA and RNA, and can be manufactured synthetically in vitro or isolated from natural sources.

The term "promoter" as used herein denotes a region within a gene to which transcription factors and/or RNA polymerase can bind so as to control expression of an associated coding sequence. Promoters are commonly, but not always, located in the 5' non-coding regions of genes, upstream of the translation initiation codon. The promoter region of a gene can include one or more consensus sequences that act as recognizable binding sites for sequence specific nucleic acid binding domains of nucleic acid binding proteins. Nevertheless, such binding sites can also be located in regions outside of the promoter, for example in enhancer regions located in introns or downstream of the coding sequence.

A "regulatory gene" is a gene involved in controlling the expression of one or more other genes.

A "probiotic" is a microorganism or group of microorganisms that provides health benefits, or that is non-pathogenic, to a subject when consumed, ingested, or otherwise administered to a subject, for example, a reduction in the likelihood of relapse following cancer treatment. As used herein, the term probiotic can be used to describe, for example, probiotic bacteria and can include the bacteria described herein as well as other bacteria.

A "prebiotic" is a substance that promotes the growth, proliferation and/or survival of one or more bacteria or yeast. As used herein, the term prebiotic can be used to describe, for example, a nutritional supplement including plant fiber, or one or more of poorly-absorbed complex carbohydrates, oligosaccharides, inulin-type fructans or arabinoxylans.

A "postbiotic" is a substance derived from a probiotic organism. As used herein, the term postbiotic can be used to describe, for example, a protein expressed by one or more bacteria, a metabolic product of one or more bacteria, or media from a culture of one or more strains of bacteria.

5.1 Methods of Determining Checkpoint Blockade Associated Colitis Risk

In certain non-limiting embodiments, the present invention provides for methods of determining whether a subject receiving or potentially receiving checkpoint blockade therapy is at greater or reduced risk for developing checkpoint blockade therapy associated colitis, including developing any checkpoint blockade therapy associated colitis symptoms, developing more severe checkpoint blockade therapy associated colitis or associated symptoms, experiencing faster progression of checkpoint blockade therapy associated colitis or symptoms, or experiencing a decreased response to other colitis treatments after receiving checkpoint blockade therapy.

An increased or decreased abundance or bacteria or spores thereof or of a bacterial genetic module is determined with respect to a reference bacteria level or a reference bacterial genetic module level, which may be based on a relative abundance in the intestinal microbiome. For instance, the reference level may represent a certain percentage in the intestinal microbiome. The reference level may also be an absolute number. The reference level may be based on a prior test in the same patient, or on levels found in a patient population, such as patients who are candidates for checkpoint blockade therapy or patients with cancer who have not undergone checkpoint blockade therapy.

Accordingly, in certain non-limiting embodiments, the present invention provides for methods of identifying subjects that are at reduced risk for developing checkpoint blockade therapy associated colitis by determining whether the feces or intestinal contents of a subject contains an increased abundance of bacteria of the Bacteroidetes phylum, including but not limited to bacteria in the families Bacteroidaceae, Rikenellaceae, and Barnesiellaceae, and/or increased microbial genetic pathways involving polyamine transport and/or B vitamin biosynthesis (e.g., (riboflavin (B2), pantothenate (B5) and thiamine (B1)). An increased abundance of said bacteria, increased polyamine transport, and/or increased B vitamin biosynthesis indicates that the subject is at reduced risk for developing checkpoint blockade therapy associated colitis.

In certain other non-limiting embodiments, the present invention provides for methods of identifying subjects that are at increased risk for developing checkpoint blockade therapy associated colitis including by determining whether the feces or intestinal contents of a subject contains a decreased amount of bacteria of the Bacteroidetes phylum, including but not limited to bacteria in the families Bacteroidaceae, Rikenellaceae, and Barnesiellaceae, and/or decreased microbial genetic pathways involved in polyamine transport and/or B vitamin biosynthesis (e.g., (riboflavin (B2), pantothenate (B5) and thiamine (B1)). A decreased amount of said bacteria, decreased polyamine transport, and/or decreased B vitamin biosynthesis indicates that the subject is at increased risk for developing checkpoint blockade therapy associated colitis.

In certain non-limiting embodiments, the microbiota sample is a fecal sample or an intestinal content sample, for example, a rectal swab.

In certain non-limiting embodiments, the amount and/or type of bacteria present in a sample is determined by measuring the amount or presence of bacterial nucleic acid specific for the type of bacteria, such as 16S rRNA.

In certain non-limiting embodiments, the amount and/or type of bacteria present in a sample is determined by shotgun sequencing of bacterial DNA, PCR amplification of specific genes carried by the bacteria, quantitative PCR of transcripts expressed specifically by the bacteria, antibody based methods of bacterial detection, metabolomic detection of bacterial metabolites, proteomic detection of bacterial proteins, and/or by methods of culturing the microbiota sample.

In certain non-limiting embodiments, the microbiota sample is collected from the subject up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days after the subject has commenced checkpoint blockade therapy. In certain non-limiting embodiments, the microbiota sample is collected from the subject up to 1, 2, 3, 4 or more weeks, or up to 1, 2, 3, 4, 5, 6, 7, 8, 9, 10, 11, 12 or more months, after the subject has commenced checkpoint blockade therapy. In certain non-limiting embodiments, the microbiota sample is collected from the subject up to 1, 2, 3, 4, 5, 6, 7 or more days, or up to 1, 2, 3, 4 or more weeks, or up to 1, 2, 3, 4, 5, 6, 7, 8, 9, 10, 11, 12 or more months, before the subject receives checkpoint blockade therapy.

In certain non-limiting embodiments, a subject may be tested and identified prior to commencing checkpoint blockade therapy. A subject identified as at increased risk for developing checkpoint blockade therapy associated colitis may receive prophylactically a therapeutic agent as described herein or otherwise effective in treating colitis, may receive increased monitoring for colitis during or after checkpoint blockade therapy, may receive a decreased dose or course of checkpoint blockade therapy, or may not receive checkpoint blockade therapy. A subject identified as at a decreased risk for developing checkpoint blockade therapy associated colitis may receive decreased monitoring for colitis, particularly invasive monitoring, during and after checkpoint blockade therapy, or may receive checkpoint blockade therapy preferentially over another therapy, in combination with another therapy, at an increased dose or course, or when checkpoint blockade therapy is expected to be beneficial, but is not indicated if colitis is likely to develop.

In certain non-limiting embodiments, a subject may be tested and identified after commencing checkpoint blockade therapy. A subject identified as at increased risk for developing checkpoint blockade therapy associated colitis may cease checkpoint blockade therapy, may receive prophylactically a therapeutic agent as described herein or otherwise effective in treating colitis, may receive increased monitoring for colitis for the duration of checkpoint blockade therapy and after such therapy, or may receive a decreased dose or course of checkpoint blockade therapy. A subject identified as at a decreased risk for developing checkpoint blockade therapy associated colitis may receive decreased monitoring for colitis, particularly invasive monitoring, for the duration of checkpoint blockade therapy and afterwards, or may continue checkpoint blockade therapy, particularly while another therapy is ceased, may receive an increased dose or course of checkpoint blockade therapy, or may continue checkpoint blockade therapy when it would not be indicated if colitis is likely to develop.

In certain non-limiting embodiments, a subject with colitis may be tested and identified prior to commencing checkpoint blockade therapy. A subject identified as at increased risk for developing checkpoint blockade therapy associated colitis may receive monitoring to determine if checkpoint blockade therapy associated colitis has contributed to the pre-existing colitis, may receive increased monitoring for progression of colitis, may receive prophylactically a therapeutic agent as described herein or otherwise effective in treating colitis, may receive a decreased dose or course of checkpoint blockade therapy, or may not receive checkpoint blockade therapy. A subject identified as at decreased risk for developing checkpoint blockade therapy associated colitis may receive monitoring of colitis consistent with the pre-existing diagnosis or may receive decreased monitoring for colitis, particularly invasive monitoring, during and after checkpoint blockade therapy, receive checkpoint blockade therapy preferentially over another therapy or in combination with another therapy, particularly another therapy associated with colitis, or may receive checkpoint blockade therapy at an increased dose or course, or when checkpoint blockade therapy is expected to be beneficial, but is not indicated if colitis is likely to develop. In both subjects at increased risk or developing checkpoint blockade therapy associated colitis and subjects at decreased risk, methods described herein may be used to determine if any progression of colitis is likely attributed to the checkpoint blockade therapy or another cause.

In certain non-limiting embodiments, a subject with colitis may be tested and identified after commencing checkpoint blockade therapy. A subject identified as at increased risk for developing checkpoint blockade therapy associated colitis may receive monitoring to determine if checkpoint blockade therapy associated colitis has contributed to the pre-existing colitis, may receive increased monitoring for progression of colitis, may receive prophylactically a therapeutic agent as described herein or otherwise effective in treating colitis, may receive a decreased dose or course of checkpoint blockade therapy, or may cease receiving checkpoint blockade therapy. A subject identified as at decreased risk for developing checkpoint blockade therapy associated colitis may receive monitoring of colitis consistent with the pre-existing diagnosis or may receive decreased monitoring for colitis, particularly invasive monitoring, during and after checkpoint blockade therapy, receive checkpoint blockade therapy preferentially over another therapy or in combination with another therapy, particularly another therapy associated with colitis, or may receive checkpoint blockade therapy at an increased dose or course, or may continue checkpoint blockade therapy when it would not be indicated if colitis is likely to develop. In both subjects at increased risk or developing checkpoint blockade therapy associated colitis and subjects at decreased risk, methods described herein may be used to determine if any progression of colitis after commencing checkpoint blockade therapy is likely attributed to the checkpoint blockade therapy or another cause.

5.2 Therapeutic Bacteria

In certain non-limiting embodiments, the compositions described herein include one or more therapeutic bacteria, or spores thereof, for example, a member of the Bacteroidetes phylum and three of its families (Bacteroidaceae, Rikenellaceae, and Barnesiellaceae), a combination thereof, or a cluster including any one or more of the foregoing bacteria.

In some non-limiting embodiments, therapeutic bacteria may have a bacterial genetic module for polyamine transport and/or B vitamin biosynthesis, particularly riboflavin (B2 vitamin), pantothenate (B5 vitamin) and thiamine (B1 vitamin) biosynthesis. Such bacterial genetic module may be entirely natively occurring, or the therapeutic bacteria may include recombinant cells as described below.

In various non-limiting embodiments of the invention, bacteria may be administered in the vegetative or dormant state, or as spores, or a mixture thereof.

In certain non-limiting embodiments, the therapeutic bacteria described herein can be modified, for example, by introducing one or more exogenous nucleic acids into the bacteria, thereby producing recombinant bacteria. Such nucleic acids can include, for example, an antibiotic resistance gene and/or an antibiotic susceptibility gene. Such recombinant bacteria can be prepared as described herein.

In certain non-limiting embodiments, therapeutic bacteria as described herein, any combinations thereof, or a cluster including any one or more of the therapeutic bacteria, may be administered in the form of purified bacteria or spores or other progenitors thereof, or alternatively may be administered as a constituent in a mixture of types of bacteria, optionally including one or more species or cluster of additional bacteria, for example, probiotic bacteria, a probiotic yeast, prebiotic, postbiotic and/or antibiotic.

In non-limiting embodiments, the present invention provides for pharmaceutical compositions, and therapeutic uses thereof, as described herein, including such forms of therapeutic bacteria, a combination thereof, or a cluster including any one or more of the therapeutic bacteria, and optionally including one or more species or cluster of additional bacteria, for example, probiotic bacteria, a probiotic yeast, prebiotic, postbiotic and/or antibiotic.

Bacteria may be administered in the form of a liquid, a suspension, a dried (e.g., lyophilized) powder, a tablet, a capsule, or a suppository, and may be administered orally, nasogastrically, or rectally. In certain non-limiting embodiments, the bacteria is administered in a food product, for example, a yogurt food product. In certain non-limiting embodiments, a "food product" means a product or composition that is intended for consumption by a human or a non-human animal. Such food products include any food, feed, snack, food supplement, liquid, beverage, treat, toy (chewable and/or consumable toys), meal substitute or meal replacement.

In certain non-limiting embodiments, the present invention provides for a composition including an isolated therapeutic bacteria, a combination of any isolate therapeutic bacteria with one another, or a cluster including any one or more of the isolated therapeutic bacteria. In some non-limiting embodiments, the bacteria is in a formulation for administration to a subject.

In other non-limiting embodiments, the composition includes one, two, three, four, five, six, seven, eight, nine, ten, eleven, twelve, thirteen, fourteen, fifteen, sixteen, seventeen, eighteen, nineteen, twenty, or between twenty and one hundred distinct types of therapeutic bacteria.

In certain non-limiting embodiments, the present invention provides for a composition including an isolated therapeutic bacteria.

In some non-limiting embodiments, said bacteria is one or more of the therapeutic bacteria described herein, but alternate or additional bacteria may be included in the compositions described herein, for example, bacteria which may be naturally occurring bacteria that are in a cluster with any one or more of therapeutic bacteria.

5.3 Recombinant Cells

The present invention provides for therapeutic compositions, and therapeutic uses thereof, as described herein, that are based on a bacterial genetic module polyamine transport and/or B vitamin biosynthesis, particularly riboflavin (B2 vitamin), pantothenate (B5 vitamin) and thiamine (B1 vitamin) biosynthesis, including such a bacterial genetic module from a bacteria of the Bacteroidetes phylum, including but not limited to bacteria in the families Bacteroidaceae, Rikenellaceae, and Barnesiellaceae. Such therapeutic compositions can include, for example, therapeutic bacteria, small molecules, polypeptides, or nucleic acid molecules.

In certain non-limiting embodiments, the therapeutic compositions treat checkpoint blockade therapy associated colitis.

In some non-limiting embodiments, the therapeutic composition includes a recombinant therapeutic bacteria, a combination thereof, or a cluster including any one or more of the therapeutic bacteria, or progeny thereof.

In certain non-limiting embodiments, the therapeutic composition includes a recombinant cell, or progeny thereof, for example, a recombinant cell expressing one or more recombinant proteins from a bacterial genetic module polyamine transport and/or B vitamin biosynthesis, particularly riboflavin (B2 vitamin), pantothenate (B5 vitamin) and thiamine (B1 vitamin) biosynthesis, including bacteria of the Bacteroidetes phylum, including but not limited to bacteria in the families Bacteroidaceae, Rikenellaceae, and Barnesiellaceae.

Delivery of nucleic acid into a subject or cell, e.g., bacterial cells of the intestinal microbiota, can be either direct, in which case the subject or cell, e.g., bacterial cells of a subject's intestinal microbiota, is directly exposed to the nucleic acid or nucleic acid-carrying vectors, or indirect, in which case, cells, e.g., a host cell, such as isolated bacterial cells of the intestinal microbiota, are first transformed with the nucleic acids in vitro, then transplanted into the subject. These two approaches are known, respectively, as in situ or ex vivo gene therapy.

For general reviews of the methods of gene therapy, see Kron and Kreppel, Curr Gene Ther 12(5):362-73 (2012); Yi et al. Curr Gene Ther 11(3):218-28 (2011); Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); Morgan and Anderson, Ann. Rev. Biochem. 62:191-217 (1993); and May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In certain non-limiting embodiments, the nucleic acid can be introduced into cells, e.g., bacterial host cells, prior to administration in vivo of the resulting recombinant cell by any method known in the art, including but not limited to transfection, electroporation, microinjection, lipofection, calcium phosphate mediated transfection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985)), and can be used in accordance with the present disclosure, provided that the necessary developmental and physiological functions of the recipient cells are not disrupted. Usually, the method of transfer includes the transfer of a selectable marker to the host cells. The cells are then placed under selection to isolate those host cells that have taken up and are expressing the transferred gene. Those host cells are then delivered to a patient.

The resulting recombinant cells, or progeny thereof, can be delivered to a patient by various methods known in the art. The amount of cells envisioned for use depends on the desired effect, patient state, etc., and can be determined by one skilled in the art.

In certain non-limiting embodiments, the terms "vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc. A "therapeutic vector" as used herein refers to a vector which is acceptable for administration to an animal, and particularly to a human.

Vectors typically include the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can accept additional (foreign) DNA and which can be introduced into a suitable host cell. A plasmid vector can contain coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA can be from the same gene or from different genes, and can be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET plasmids (Invitrogen, San Diego, Calif.), pCDNA3 plasmids (Invitrogen), pREP plasmids (Invitrogen), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

Suitable vectors include, for example, bacteriophages, cosmids, plasmids, naked DNA, DNA lipid complexes, and other recombination vehicles typically used in the art which have been described for expression in a variety of eukaryotic and prokaryotic hosts, and can be used for gene therapy as well as for simple protein expression.

5.4 Pharmaceutical Compositions

In certain non-limiting embodiments, the present disclosure provides for pharmaceutical compositions, and therapeutic uses thereof as described herein, which include a therapeutic composition, as described herein, such as, for example, a therapeutic bacteria, as described herein. Such pharmaceutical compositions can further include at least one other agent, such as a stabilizing compound or additional therapeutic agent, for example, a probiotic, prebiotic, postbiotic, and/or antibiotic, and can be administered in any sterile, biocompatible pharmaceutical carrier, including, but not limited to, saline, buffered saline, dextrose, glycerol, polyethylene glycol, and water. The composition can be in a liquid or lyophilized or freeze-dried form. In some non-limiting embodiments, a formulation includes a diluent (for example, a buffer such as Tris, citrate, acetate or phosphate buffers) having suitable pH values and ionic strengths, solubilizer such as polysorbate (e.g., Tween®), carriers such as human serum albumin or gelatin. In some cases, a preservative may be included that does not affect viability of the organisms in the composition. Examples of preservatives include thimerosal, parabens, benzylalconium chloride or benzyl alcohol, antioxidants such as ascorbic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in Remington's Pharmaceutical Sciences, 18th ed. A. R. Gennaro, ed. Mack, Easton, Pa. (1980).

In certain non-limiting embodiments, the methods and compositions of the present disclosure find use in treating checkpoint blockade therapy associated colitis in a subject. Such therapeutic bacteria are administered to the patient in a pharmaceutically acceptable carrier. The route of administration eventually chosen will depend upon a number of factors and can be ascertained by one skilled in the art.

In certain non-limiting embodiments, the pharmaceutical compositions of the present disclosure can be formulated using pharmaceutically acceptable carriers well known in the art in dosages suitable for oral, nasogastric, or rectal administration. Such carriers enable the pharmaceutical compositions to be formulated as tablets, pills, capsules, liquids, gels, syrups, slurries, suspensions and the like, for oral, rectal or nasal ingestion by a patient to be treated. In some non-limiting embodiments, the formulation includes a capsule or tablet formulated for gastrointestinal delivery, e.g., an enteric coated capsule or pill.

Pharmaceutical compositions suitable for use in the present disclosure include, in certain non-limiting embodiments, compositions where the active ingredients are contained in an effective amount to achieve the intended purpose. The amount will vary from one individual to another and will depend upon a number of factors, including the intestinal microbiota of the subject, whether the patient has already commenced or ceased checkpoint blockade therapy, the type and dose of checkpoint blockade therapy, whether the patient has colitis other than checkpoint blockage therapy associated colitis, whether the patient already has checkpoint blockade therapy associated colitis, the grade or severity of any colitis, the patient's medical need for checkpoint blockade therapy, the results of any methods described herein to asses the risk of the patient in developing or experience an increase in severity or of more severe checkpoint blockade therapy associated colitis, and the overall physical condition of the patient.

In certain non-limiting embodiments, the compositions of the present disclosure can be administered for therapeutic treatments, which may include prophylactic treatments. For example, in alternative non-limiting embodiments, pharmaceutical compositions of the present disclosure are administered in an amount sufficient to treat, prevent and/or ameliorate checkpoint therapy associated colitis, for example, onset of colitis, increase in severity of pre-existing colitis, onset of one or more colitis symptoms, and/or increase in severity of one or more colitis symptoms. As is well known in the medical arts, dosages for any one patient depends upon many factors, including stage of the disease or condition, the severity of the disease or condition, the patient's size, body surface area, age, the particular compound to be administered, sex, time and route of administration, general health, and interaction with other drugs being concurrently administered.

Accordingly, in certain non-limiting embodiments, a therapeutic bacteria can be administered to a patient alone, or in combination with one or more other drugs, particularly a checkpoint blockade therapeutic agent, nucleotide sequences, lifestyle changes, etc. used in the treatment and/or prevention of colitis, particularly checkpoint blockade therapy associated colitis, and/or symptoms thereof, and/or in pharmaceutical compositions where it is mixed with excipient(s) or other pharmaceutically acceptable carriers.

Single or multiple administrations of formulations can be given depending on the dosage and frequency as required and tolerated by the patient. In certain non-limiting embodiments, the formulations should provide a sufficient quantity of active agent to effectively treat, prevent and/or ameliorate checkpoint blockade therapy associated colitis, or symptoms or complications thereof as described herein.

5.5 Methods of Treatment and Use of Therapeutic Bacteria

In certain non-limiting embodiments, the present invention provides for a method of treating checkpoint blockade therapy associated colitis. Treating, in certain non-limiting embodiments of the invention, includes preventing the onset of checkpoint blockade therapy associated colitis and/or one or more symptoms thereof, preventing an increase in severity of checkpoint blockade therapy associated colitis and/or one or more symptoms thereof, including preventing progression of checkpoint blockade therapy associated colitis or colitis at least partially resulting from checkpoint blockade therapy to a higher grade, decreasing the severity of checkpoint blockade therapy associated colitis and/or one or more symptoms thereof, including causing regression of checkpoint blockage therapy associated colitis or colitis at least partially resulting from checkpoint blockade therapy to a lower grade, and/or causing the cessation of checkpoint blockade therapy associated colitis and/or one or more symptoms thereof, including cessation of colitis at least partially resulting from checkpoint blockade therapy.

Treating, in certain non-limiting embodiments of the invention, includes administering to a subject in need of such treatment, an effective amount of a composition described herein, for example, one or more therapeutic bacteria, including, but not limited to one or more recombinant therapeutic bacteria, or a composition containing one or much such therapeutic bacteria.

In certain non-limiting embodiments, the compositions described herein include one or more members of the Bacteroidetes phylum and three of its families (Bacteroidaceae, Rikenellaceae, and Barnesiellaceae), a combination thereof, or a cluster including any one or more of the foregoing bacteria.

In some non-limiting embodiments, therapeutic bacteria may have a bacterial genetic module for polyamine transport and/or B vitamin biosynthesis, particularly riboflavin (B2 vitamin), pantothenate (B5 vitamin) and thiamine (B1 vitamin) biosynthesis. Such bacterial genetic module may be entirely natively occurring, or the therapeutic bacteria may include recombinant cells as described below.

In certain non-limiting embodiments, subjects in need of such treatment or compositions include subjects who are receiving or may receive checkpoint blockade therapy. Such subjects typically include patients with certain cancers and infectious diseases. In certain non-limit embodiments, subjects in need of such treatment or compositions have checkpoint blockade therapy associated colitis, colitis at least partially associated with checkpoint blockade therapy, or colitis not associated with checkpoint blockade therapy. In some non-limiting embodiments, subjects in need of such treatment or compositions have an increased risk of developing checkpoint blockade therapy colitis and/or of experiencing more severe checkpoint blockade therapy colitis. In some non-limiting embodiments, such risk is assessed using methods and compositions described herein.

In certain non-limiting embodiments, the present invention provides for a method of treating checkpoint blockade therapy associated colitis by administering, to a subject in need of such treatment, an effective amount of a probiotic including at least one therapeutic bacteria. In certain non-limiting embodiments, the probiotic includes endogenous flora (for example, an autologous fecal microbiota transplant) that are re-introduced into the subject.

In certain non-limiting embodiments, the present invention provides for a method of treating checkpoint blockade therapy associated colitis by administering, to a subject in need of such treatment, an effective amount of a prebiotic including a therapeutic bacteria. In certain non-limiting embodiments, the prebiotic may be administered separately from the therapeutic bacteria. The prebiotic promotes the growth, proliferation and/or survival of at least one therapeutic bacteria.

The prebiotic may include one or more agents, for example, a nutritional supplement, that increases growth and survival of at least one therapeutic bacteria. In certain non-limiting embodiments, the prebiotic includes one or more of poorly-absorbed complex carbohydrates, oligosaccharides, inulin-type fructans or arabinoxylans.

In certain non-limiting embodiments, the present invention provides for a method of treating checkpoint blockade therapy associated colitis by administering, to a subject in need of such treatment, an effective amount of a postbiotic including a therapeutic bacteria. In certain non-limiting embodiments, the postbiotic may be administered separately from the therapeutic bacteria. In certain non-limiting embodiments, the postbiotic includes one or more agents, such as a protein, expressed by the therapeutic bacteria. In certain non-limiting embodiments, the postbiotic includes bacterial metabolites that treat or help treat checkpoint blockade therapy associated colitis.

In certain non-limiting embodiments, the present invention provides for a method of treating checkpoint blockade associated colitis including determining checkpoint blockade therapy associated risk as described herein. The method may further include determining any change in checkpoint blockade therapy associated risk over time in the subject. In certain non-limiting embodiments, the present invention provides a method of treating checkpoint blockade associated colitis including assessing the grade or severity of colitis in the subject treated.

In certain non-limiting embodiments, the present invention provides the use of any composition described herein, including the use of any therapeutic bacteria described herein for treating checkpoint blockade therapy associated colitis in a subject. The use may be further characterized by aspects of the methods described above and elsewhere herein.

5.6 Kits

The presently disclosed subject matter provides for kits for diagnosing a subject receiving or potentially receiving checkpoint blockade therapy is at greater or reduced risk for developing checkpoint blockade therapy associated colitis, including developing any checkpoint blockade therapy associated colitis symptoms, developing more severe checkpoint blockade therapy associated colitis or associated symptoms, experiencing faster progression of checkpoint blockade therapy associated colitis or symptoms, or experiencing a decreased response to other colitis treatments after receiving checkpoint blockade therapy.

In certain non-limiting embodiments, the kit includes an agent for determining whether the feces or intestinal contents of a subject contains an increased abundance of bacteria of the Bacteroidetes phylum, including but not limited to bacteria in the families Bacteroidaceae, Rikenellaceae, and Barnesiellaceae, and/or increased microbial genetic pathways involving polyamine transport and/or B vitamin biosynthesis (e.g., (riboflavin (B2), pantothenate (B5) and thiamine (B1)).

In certain non-limiting embodiments, the agent includes nucleic acid primers specific for said bacteria. In certain non-limiting embodiments, the nucleic acid primers are specific for 16S rRNA sequencing.

The presently disclosed subject matter provides for kits for treating a subject who has received or may receive checkpoint blockade therapy. In certain non-limiting embodiments, the kit includes one or more therapeutic bacteria or compositions as described herein.

In certain non-limiting embodiments, the kit includes instructions for administering the therapeutic bacteria or compositions. The instructions can include information about the use of the therapeutic bacterial or compositions for treating checkpoint blockade therapy associated colitis. In certain non-limiting embodiments, the instructions include at least one of the following: description of the therapeutic bacteria or composition; dosage schedule and administration; precautions; warnings; indications; counter-indications; over dosage information; adverse reactions; animal pharmacology; clinical studies; and/or references. The instructions can be printed directly on a container (when present) containing the therapeutic bacteria or composition, or as a label applied to the container, or as a separate sheet, pamphlet, card, or folder supplied in or with the container.

In certain non-limiting embodiments, the kit may include both components for diagnosing a subject receiving or potentially receiving checkpoint blockade therapy is at greater or reduced risk for developing checkpoint blockade therapy associated colitis and components for treating a subject who has received or may receive checkpoint blockade therapy. The kit may include instructions for administering components for treating the subject based upon results obtained using the components for diagnosing the subject.

6. WORKING EXAMPLES

The presently disclosed subject matter will be better understood by reference to the following Examples, which are provided as exemplary of the invention, and not by way of limitation.

Checkpoint blockade therapy may be referred to in these examples as "CTL4 blockade."

6.1 Methods—Specimen DNA Preparation, Sequencing, and Statistical Analyses

The following methods were used in connection with the remaining examples.

6.1(a) Study Patients and Specimen Collection from Patients Receiving Checkpoint Blockade Therapy Fecal samples of 34 adult patients diagnosed with metastatic melanoma who received ipilimumab checkpoint blockade therapy at Memorial Sloan-Kettering Cancer Center (MSKCC) were collected. For 30 patients, fecal samples were collected from each patient prior to the first administration of ipilimumab; for 2 patients who developed gastrointestinal inflammation and 2 who remained inflammation free, samples were collected after administration of ipilimumab commenced, but before onset of colitis. Toxicities were graded retrospectively by a single investigator based upon chart review using CTCAE, version 4.0 and grading on the terms diarrhea and colitis. Patients were assigned a colitis score based upon the following: no diarrhea (score 0), grade 1 diarrhea (score 1), grade 2 diarrhea (score 2), grade 2 diarrhea and/or grade 2 colitis (all 3 cases had both grade 2 diarrhea and grade 2 colitis) (score 3), grade 3 diarrhea and/or grade 3 colitis (1 case with both grade 3 diarrhea and grade 3 colitis) (score 4). All participants provided written consent for specimen collection and analysis under the study protocol approved by the MSKCC Institutional Review Board.

Subjects had no previous history of colitis and bowel resection, and had not received antibiotic treatment in the preceding 2 months. Patients were excluded from analysis if the first fecal sample was collected after the onset of colitis, if the patient did not receive ipilimumab, or if colitis status was unknown. Ipilimumab monotherapy was administered at a dose of 3 mg/kg every 3 weeks for up to 4 doses, with three exceptions. Patients #10 and #15 received vemurafenib before and during ipilimumab treatment as part of a clinical trial. Patient #13 was part of a blinded clinical trial and received ipilimumab at either 3 mg/kg or 10 mg/kg. A small number of patients (Progressed-to-Colitis, n=2; Colitis-Free, n=3) received additional doses of ipilimumab either as part of maintenance treatment (every 3 months) on a clinical study or as part of a second course of ipilimumab; however, the colitis cases documented here occurred before this additional dosing was administered. Systemic cancer treatment administered prior to (n=14) or during (n=2) ipilimumab therapy was determined retrospectively upon chart review by a single investigator (MKC).

6.1(b) DNA Extraction

Each fecal sample was immediately snap-frozen at −80 C and subsequently subjected to bead beating and phenol chloroform extraction for DNA purification. Samples were resuspended in 500 μl of an extraction buffer (200 mM Tris, pH 8.0/200 mM NaCl/20 mM EDTA), 200 μl of 20% SDS, 500 μl of phenol:chloroform:isoamyl alcohol (24:24:1), and 500 μl of 0.1 mm diameter zirconia/silica beads (BioSpec Products). For 2 min, cells were lysed by mechanical disruption using a bead beater. DNA was extracted in a phenol/chloroform/isoamyl solution twice and precipitated with ethanol and sodium acetate. DNA was resuspended in 200 μl of TE buffer containing 100 ug/ml RNase and further purified using QIAmp Mini Spin Columns (Qiagen). After eluting the sample in 100 μl of distilled water, double-stranded DNA was quantified.

6.1(c) 16S rRNA Gene Amplification and Multiparallel Sequencing

The V4-V5 region of the 16S rRNA gene was amplified and sequenced on an Ilumina MiSeq platform. For each fecal sample, replicate PCR reactions were performed using modified universal bacterial primers designed to amplify the V4-V5 16S rRNA region: 563F (59-nnnnnnnn-NNNNNNNNNNNN-AYTGGGYDTAAAGN G-39) (SEQ. ID. No.:1) and 926R (59-nnnnnnnn-NNNNNNNNNNNN-CCGTCAATTYHTTTR AGT-39) (SEQ. ID. No.:2). Each reaction contained 50 ng of purified DNA, 0.2 mM dNTPs, 1.5 uM MgCl2, 1.25 U Platinum TaqDNA poly-merase, 2.5 µl of 10×PCR buffer, and 0.2 µM of each primer. A unique 12-base Golay barcode (Ns) preceded the primers for sample identification after pooling amplicons. One to eight additional nucleotides were added before the barcode to offset the sequencing of the primers. Cycling conditions were the following: 94° C. for 3 min, followed by 27 cycles of 94° C. for 50 sec, 51° C. for 30 sec, and 72° C. for 1 min, where the final elongation step was performed at 72° C. for 5 min. Replicate PCRs were combined and were subsequently purified using the Qiaquick PCR Purification Kit (Qiagen) and Qiagen MinElute PCR Purification Kit (Qiagen). Using the Illumina TruSeq Sample Preparation procedure, PCR products were quantified and pooled at equimolar amounts before Illumina barcodes and adaptors were ligated on. The completed library was sequenced on an Ilumina Miseq platform according to the Illumina recommended protocol.

6.1(d) Accession Numbers

The 16S rRNA gene sequences and shotgun sequences (forward R1, reverse R2) analysed herein have been deposited in the NCBI SRA database under the BioProject ID: PRJNA302832.

The associated BioSamples' accession numbers are the following: SAMN04281019, SAMN04281020, SAMN04281021, SAMN04281022, SAMN04281023, SAMN04281024, SAMN04281025, SAMN04281026, SAMN04281027, SAMN04281028, SAMN04281029, SAMN04281030, SAMN04281031, SAMN04281032, SAMN04281033, SAMN04281034, SAMN04281035, SAMN04281036, SAMN04281037, SAMN04281038, SAMN04281039, SAMN04281040, SAMN04281041, SAMN04281042, SAMN04281043, SAMN04281044, SAMN04281045, SAMN04281046, SAMN04281047, SAMN04281048, SAMN04281049, SAMN04281050, SAMN04281051, SAMN04281052 ‖ SAMN04281200, SAMN04281201, SAMN04281202, SAMN04281203, SAMN04281204, SAMN04281205, SAMN04281206, SAMN04281207, SAMN04281208, SAMN04281209, SAMN04281210, SAMN04281211, SAMN04281212, SAMN04281213, SAMN04281214, SAMN04281215, SAMN04281216, SAMN04281217, SAMN04281218, SAMN04281219, SAMN04281220, SAMN04281221, SAMN04281222, SAMN04281223, SAMN04281224, SAMN04281225, SAMN04281226, SAMN04281227, SAMN04281228, SAMN04281229, SAMN04281230, SAMN04281231, SAMN04281232, SAMN04281233, SAMN04281234, SAMN04281235, SAMN04281236, SAMN04281237, SAMN04281238, SAMN04281239, SAMN04281240, SAMN04281241, SAMN04281242, SAMN04281243.

6.1(e) DNA Sequence Analysis

The DNA sequences were analyzed using mothur version 1.31.1. Sequences were aligned using the Silva reference alignment as a template and potentially chimeric sequences were eliminated using the UChime algorithm. 5000 sequences per patient were selected (mean, 4974; SD, 150) and sequences with a distance-based similarity of 97% or greater were grouped into OTUs using the furthest-neighbor algorithm. OTUs were classified using the Greengenes 16S rRNA reference database.

OTU-based microbial diversity was estimated by calculating two diversity indexes, Shannon and Inverse Simpson. OTU-based richness was determined by calculating the Chao richness estimate and constructing rarefaction curves.

OTUs were grouped at different levels of classification (phylum, class, order, family, genus); at each level, OTUs that did not have a classification were grouped together by the highest available resolution (e.g. at the genus level, an OTU classified as p_Bacteroidetes_c_Bacteroidia_o_Bacteroidales_f_Barnesiellaceae_unclassifed was grouped as f_Barnesiellaceae_unclassifed). Feature selection of the intestinal microbia's composition was performed on OTUs with an average abundance greater than 0.01% in either patient group (Progressed-to-Colitis or Colitis-Free) and grouped by phylotype.

6.1(f) Shotgun Sequencing and Metabolic Pathway Reconstruction

Stool samples from all 10 Progressed-to-Colitis (PtC) patients and 12 Colitis-Free (C-F) patients were subjected to shotgun sequencing. C-F patient samples were chosen so that the full spectrum of Bacteroidetes phylum abundance was represented. Libraries were constructed with Illumina barcodes from the TruSeq DNA Sample Prep kit (Illumina) and reagents from KAPA Library Preparation kit (Kapa Biosystems), and then sequenced on an Illumina MiSeq platform using 2×250 nucleotide paired-end sequencing, according to the manufacturer's instructions. Sequencing reads were converted into relative abundances of microbial metabolic modules using HUMAnN, the Human Microbiome Project metabolic reconstruction pipeline, and mapped to the Kyoto Encyclopedia of Genes and Genomes (KEGG). Relative species abundances were calculated by the MetaPhlAn pipeline.

6.1(g) Statistics

Statistical analyses of intestinal microbiota samples were performed using R Statistical Language (v3.1.1) and GraphPad Prism (version 6.0e) software packages. Unpaired Mann-Whitney rank sum test (two-tailed) was used for comparisons of continuous variables between two groups. Bar plots were used to represent the data's mean at the center values, with error bars to indicate standard deviation. Spearman rank correlation tests (two-tailed) were used to find significant correlations between two continuous variables. Linear discriminant analysis effect size (LEfSe) was used to identify differentially abundant features between classes of samples. Recursive partitioning to form classification trees was performed in R using the packages rpart. Generalized linear model (using probit regression and the glm R-function) was constructed on all combinations of the following five genetic modules associated with Colitis-Free patients: Polyamine transport system (M299), Riboflavin biosynthesis (M125), Pantothenate biosynthesis (M119), Thiamine biosynthesis (M127) and Biotin biosynthesis (M123). Leave-one-out cross-validation was used to compute model sensitivity and specificity. Unadjusted p-values less than 0.05 were considered to be significant for the Mann-Whitney rank sum test and Spearman rank correlation tests.

6.2 Colitis Development in Patients Receiving Checkpoint Blockade Therapy

Experimental data confirmed that present or absence of microbiota from the Bacteroidetes phylum and certain bacterial genetic modules sometimes found in members of that phylum are predictive of checkpoint blockade therapy associated colitis development. Microbiota from the Bacteroidetes phylum and certain bacterial genetic modules sometimes found in members of that phylum were found to correlate with protection against checkpoint blockade therapy associated colitis.

6.2(a) Colitis Development in Patients Following CTLA-4-Blockade

To correlate pre-colitis fecal composition with the subsequent development of checkpoint blockade associated colitis, the intestinal microbiota of 34 patients was analyzed. Patients who did not develop gastrointestinal inflammation following CTLA-4 blockade are herein referred to as Colitis-Free (C-F), and patients who experienced inflammatory complications after CTLA-4 blockade are referred to as having Progressed to Colitis (PtC).

Patients were assigned a colitis score by retrospective chart review, which ranged from no diarrhea (score 0) in C-F patients to severe colitis (score 4) in PtC patients, as described in Example 6.1. Patient age was defined as of the first dose of ipilimumab and rounded down to the nearest integer. Patients' history of systemic cancer therapy was determined by retrospective chart review.

The patients in this study ranged in age between 28 and 85 and were diagnosed with metastatic melanoma. 40% of PtC patients and 50% of C-F patients were treated with systemic cancer therapy administered either prior to (14/16) or both before and during (2/16; both C-F) ipilimumab treatment course. In general, fecal samples were obtained from patients prior to the first dose of ipilimumab (30/34), although in patients who subsequently developed inflammation and 2 patients who remained inflammation free, samples were obtained after initiation of ipilimumab but before the onset of colitis. Of the 34 patients, 10 were diagnosed with gastrointestinal inflammation between 13 and 57 days after initiation of ipilimumab.

Patient assessment is presented in Table 1. The symbol (+) indicates treatments that are given concurrently, while symbol (;) indicates treatments administered at different times. The symbol (*) indicates systemic cancer treatment administered both before and during ipilimumab therapy. C-F patients, n=24; PtC patients, n=10.

TABLE 1

Patient Colitis Assessment

| Patient Group | Patient No. | Colitis Score | Sex | Age | Prior Systemic Cancer Treatment(s) |
|---|---|---|---|---|---|
| C-F | 1 | 0 | M | 62 | Tyrosinase DNA vaccine (in adjuvant setting) |
| C-F | 2 | 0 | F | 50 | Adjuvant Interferon |
| C-F | 3 | 0 | M | 80 | |
| C-F | 4 | 0 | M | 74 | Vemurafenib |
| C-F | 5 | 0 | F | 72 | |
| C-F | 6 | 0 | M | 68 | |
| C-F | 7 | 0 | F | 66 | |
| C-F | 8 | 0 | M | 70 | |
| C-F | 9 | 0 | F | 73 | Anti-gp75 monoclonal antibody IMC-20D7S; AZD6244; vemurafenib |
| C-F | 10 | 0 | F | 61 | *Vemurafenib |
| C-F | 11 | 0 | M | 63 | |
| C-F | 12 | 0 | M | 60 | |
| C-F | 13 | 0 | M | 69 | |
| C-F | 14 | 0 | F | 53 | Vemurafenib |
| C-F | 15 | 0 | F | 28 | *Vemurafenib |
| C-F | 16 | 0 | M | 85 | |
| C-F | 17 | 0 | F | 67 | |
| C-F | 18 | 0 | M | 63 | Cisplatin + vinblastine + temozolomide |
| C-F | 19 | 0 | M | 42 | Nivolumab (in clinical trial) |
| C-F | 20 | 0 | F | 65 | Cisplatin + vinblastine + temozolomide + RO4929097; vinblastine |
| C-F | 21 | 0 | M | 62 | |
| C-F | 22 | 0 | M | 68 | Temozolomide |
| C-F | 23 | 0 | F | 65 | |
| C-F | 24 | 0 | M | 81 | Temozolomide; AZD6224 |
| PtC | 25 | 2 | M | 76 | Vaccine, GD2L-KLH with OPT-821 |
| PtC | 26 | 3 | F | 66 | |
| PtC | 27 | 3 | M | 60 | Adjuvant Interferon |
| PtC | 28 | 4 | M | 53 | |
| PtC | 29 | 3 | M | 53 | Vemurafenib |
| PtC | 30 | 1 | F | 59 | Temozolomide |
| PtC | 31 | 1 | M | 73 | |
| PtC | 32 | 1 | F | 56 | |
| PtC | 33 | 1 | M | 73 | |
| PtC | 34 | 2 | F | 64 | |

As shown by the data in Table 1, there were no significant differences in age or gender between C-F and PtC patients. The patient population presented in Table 1 was used throughout these examples.

6.2(b) Intestinal Microflora in Patients Administered CTLA-4-Blockade

In FIG. 1A, fecal sample collection (circle) and the onset of colitis (triangle) are shown at the indicated time-points during treatment with ipilimumab, a monoclonal antibody that blocks CTLA-4-signaling. Dates are relative to first dose of ipilimumab treatment. An average abundance greater than 0.01% was used as the threshold for considering an OTU to be present within fecal samples in either patient group (OTUs, n=578); OTUs at an abundance of 0.01% or lower were not considered to be present in the patients' microbiota.

Figure 1B:
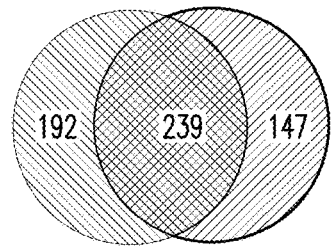
Figure 1C:
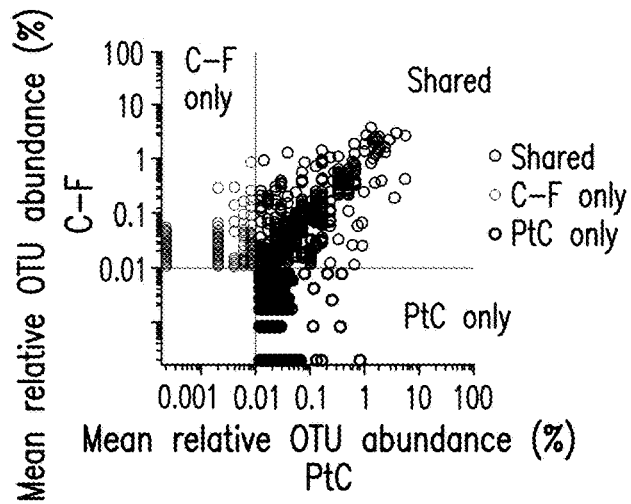

Using this definition, the number of OTUs present in C-F patients only, PtC patients only, or shared between the patient groups was calculated. Results are presented in a scaled Venn diagram (FIG. 1B). The mean relative abundance of OTUs (FIG. 1C), total abundance of OTUs (FIG. 1D), and distribution of OTUs (FIG. 1E) that are present in C-F patients only, PtC patients only or shared between the patients were also determined.

Figure 1D:
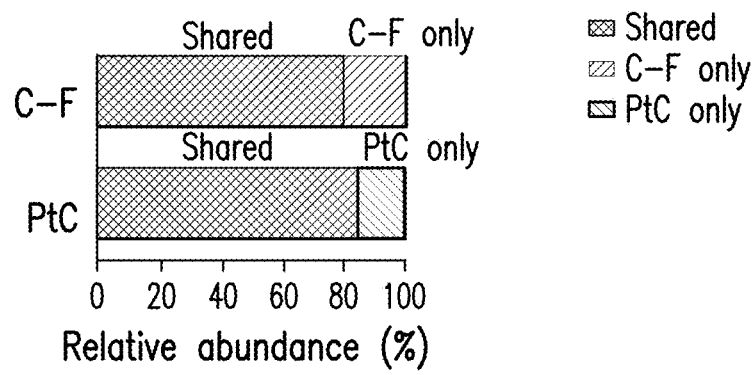
Figure 1E:
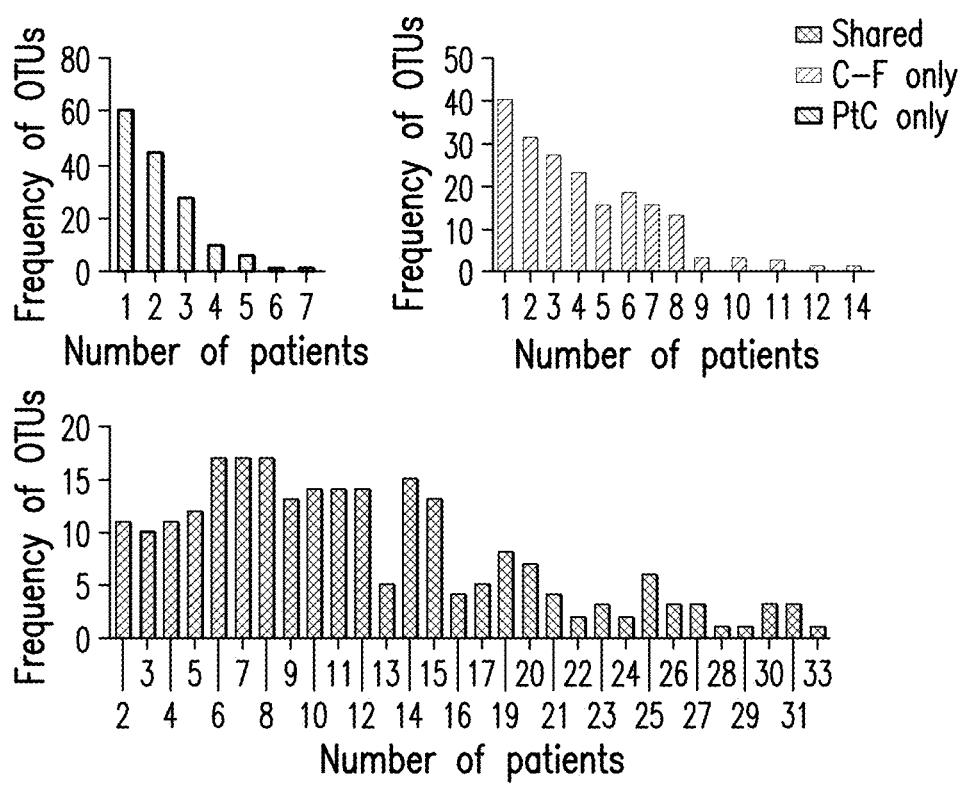

C-F and PtC patients harbored intestinal microbiota with similarly complex microbial populations and shared 239 of 578 OTUs (defined at a 97% sequence similarity) (FIG. 1B). These 239 shared OTUs represent 79% and 83% of the total OTU abundance in the C-F and PtC patient groups, respectively (FIG. 1C and FIG. 1D), and many were present in 5 or more patients (FIG. 1D). In contrast, OTUs that were either associated with only C-F or PtC patients were generally detected in fewer than 5 patients (FIG. 1E).

The OTUs that are shared between the C-F and PtC patient groups are more evenly distributed. Roughly 20% of shared OTUs are found in over half of all patients (FIG. 1E).

Figure 2A:
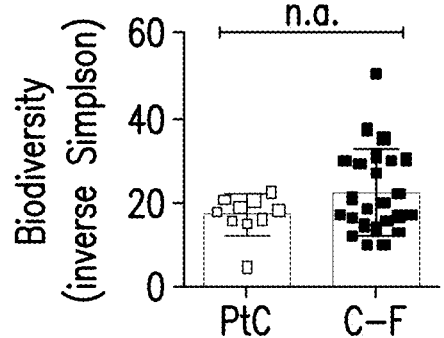
Figure 2B:
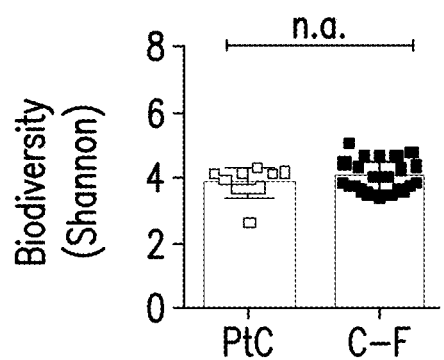
Figure 2C:
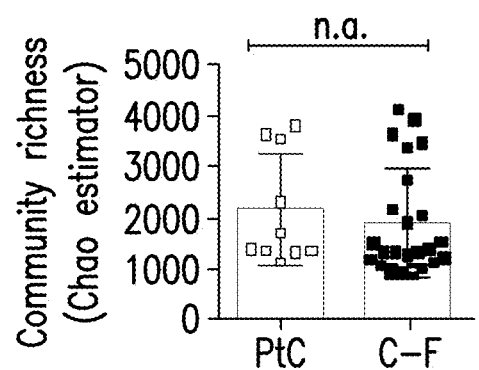
Figure 2D:
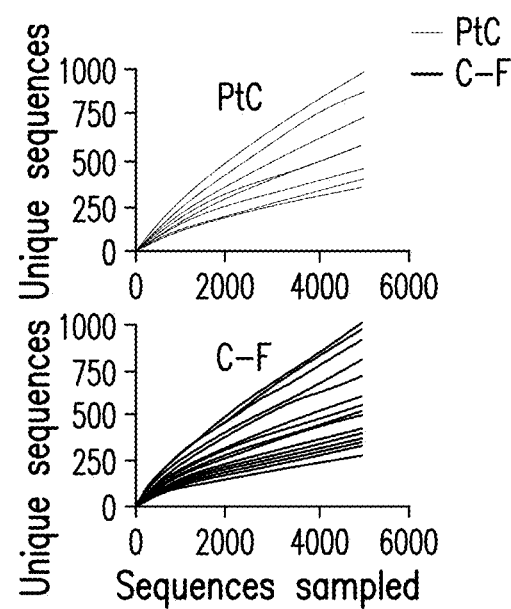

Biodiversity in each patient sample was estimated by the Inverse Simpson index (FIG. 2A) and the Shannon index (FIG. 2B). Richness was measured by the Chao estimator (FIG. 2C) and rarefaction curves (FIG. 2D) Mann-Whitney tests were used to compare microbial diversity parameters between the patient groups. These differences in the distribution of OTUs among the patient groups did not significantly impact the overall biodiversity. Microbial richness, reflecting the number of unique phylotypes within a given sample, was found to be similar between patients who developed CTLA-4 blockade associated colitis and those who remained colitis-free.

Figure 3B:
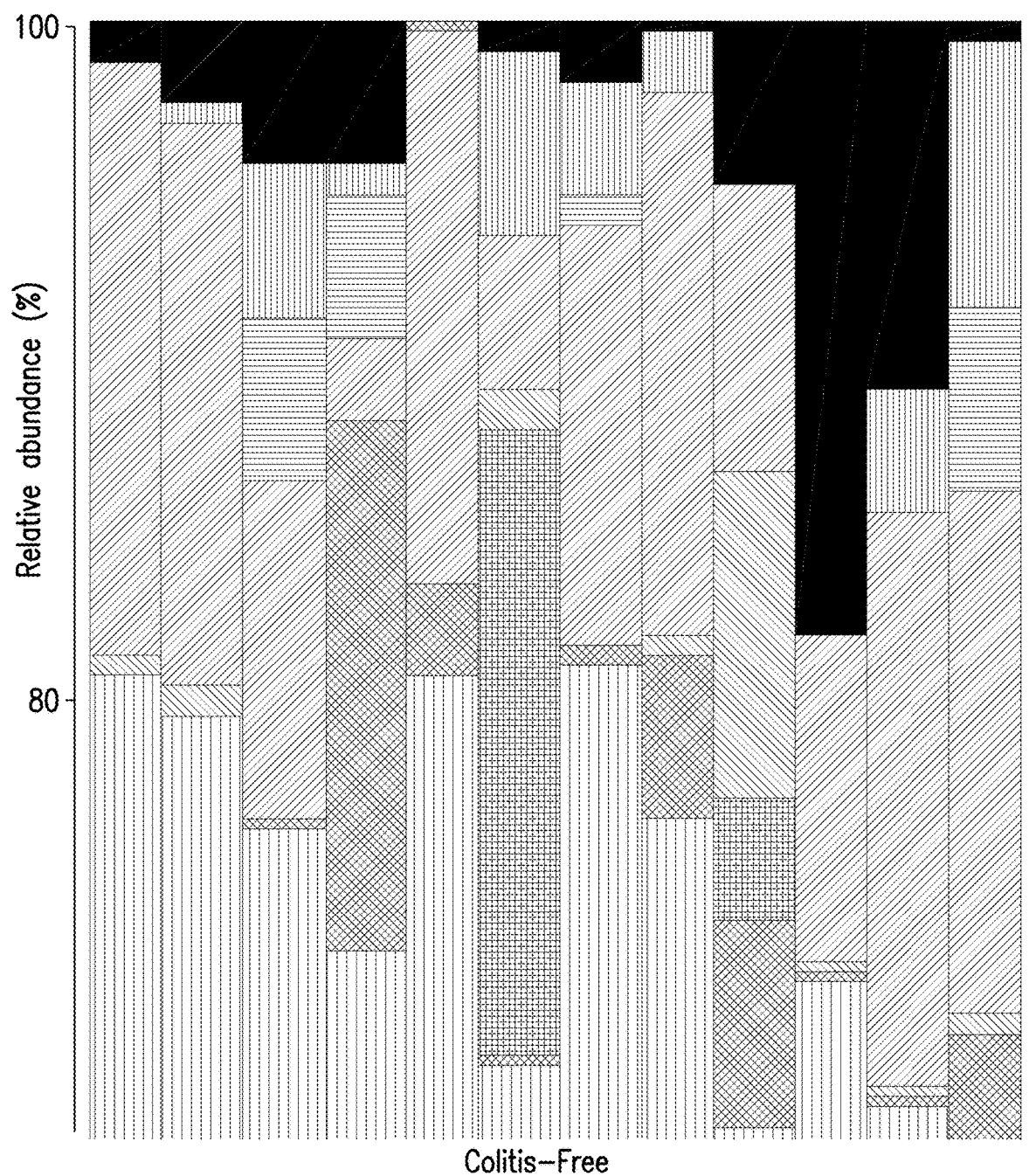
Figure 3C:
Figure 3D:
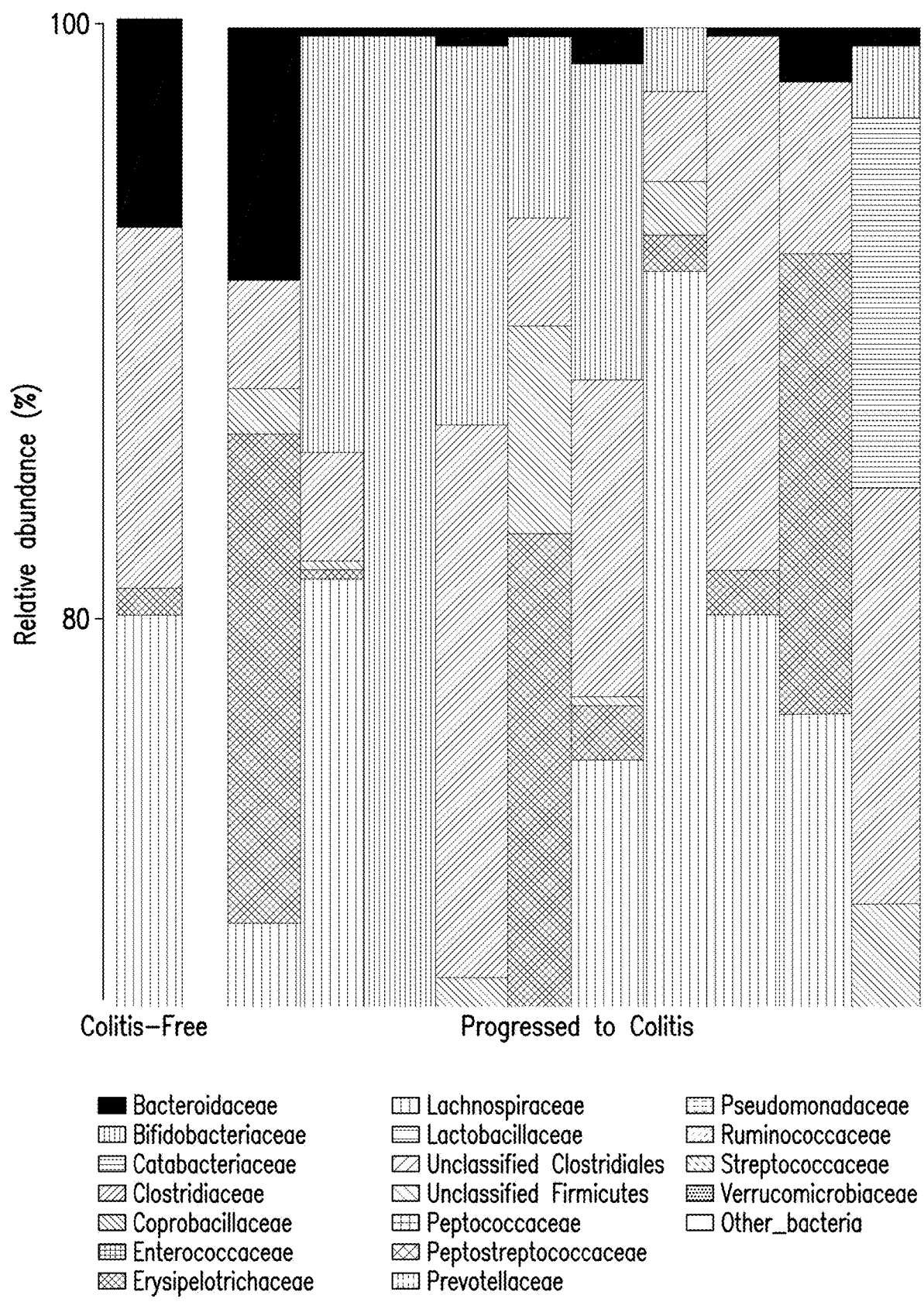
Figure 3E:
Figure 3F:
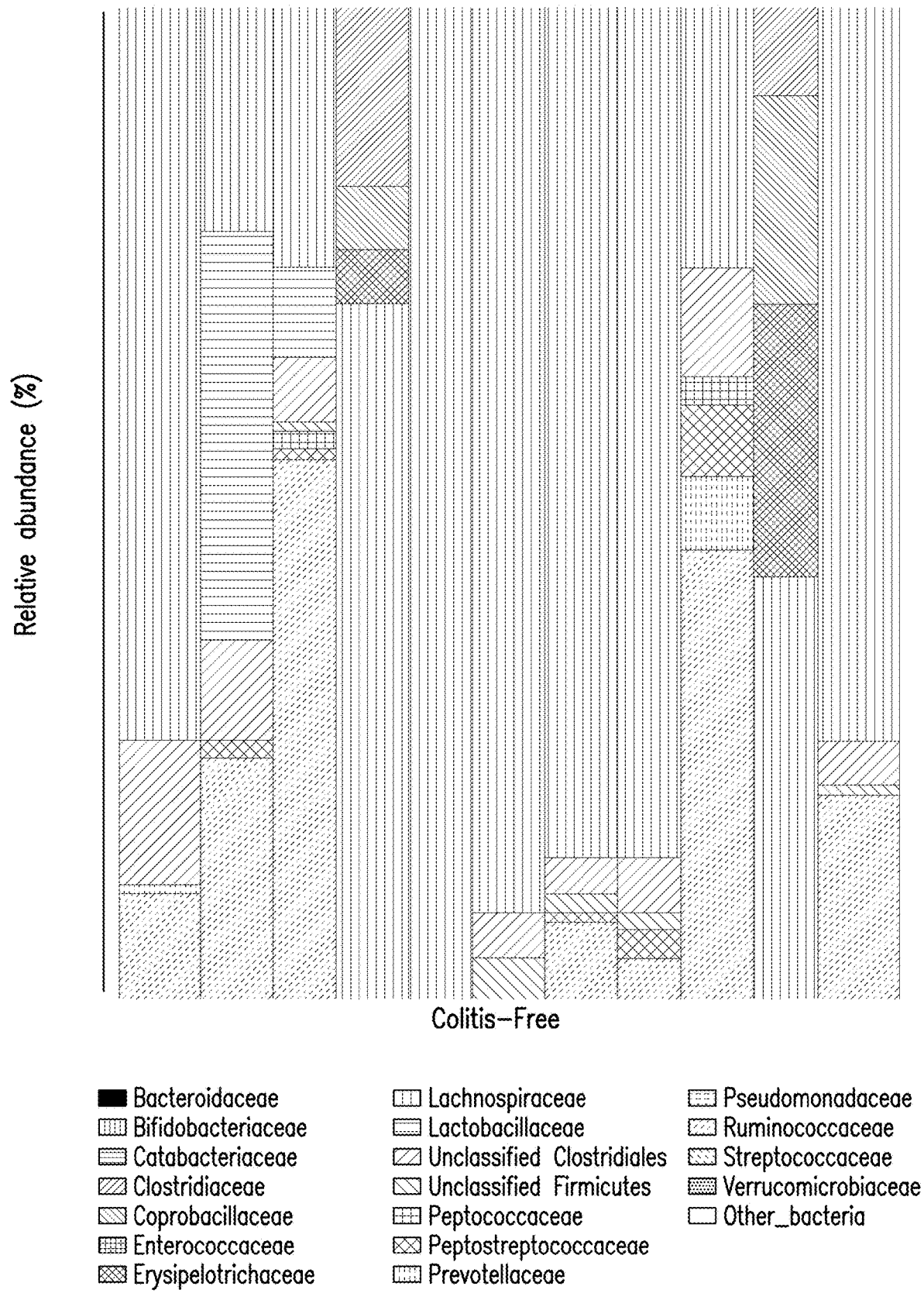
Figure 3G:
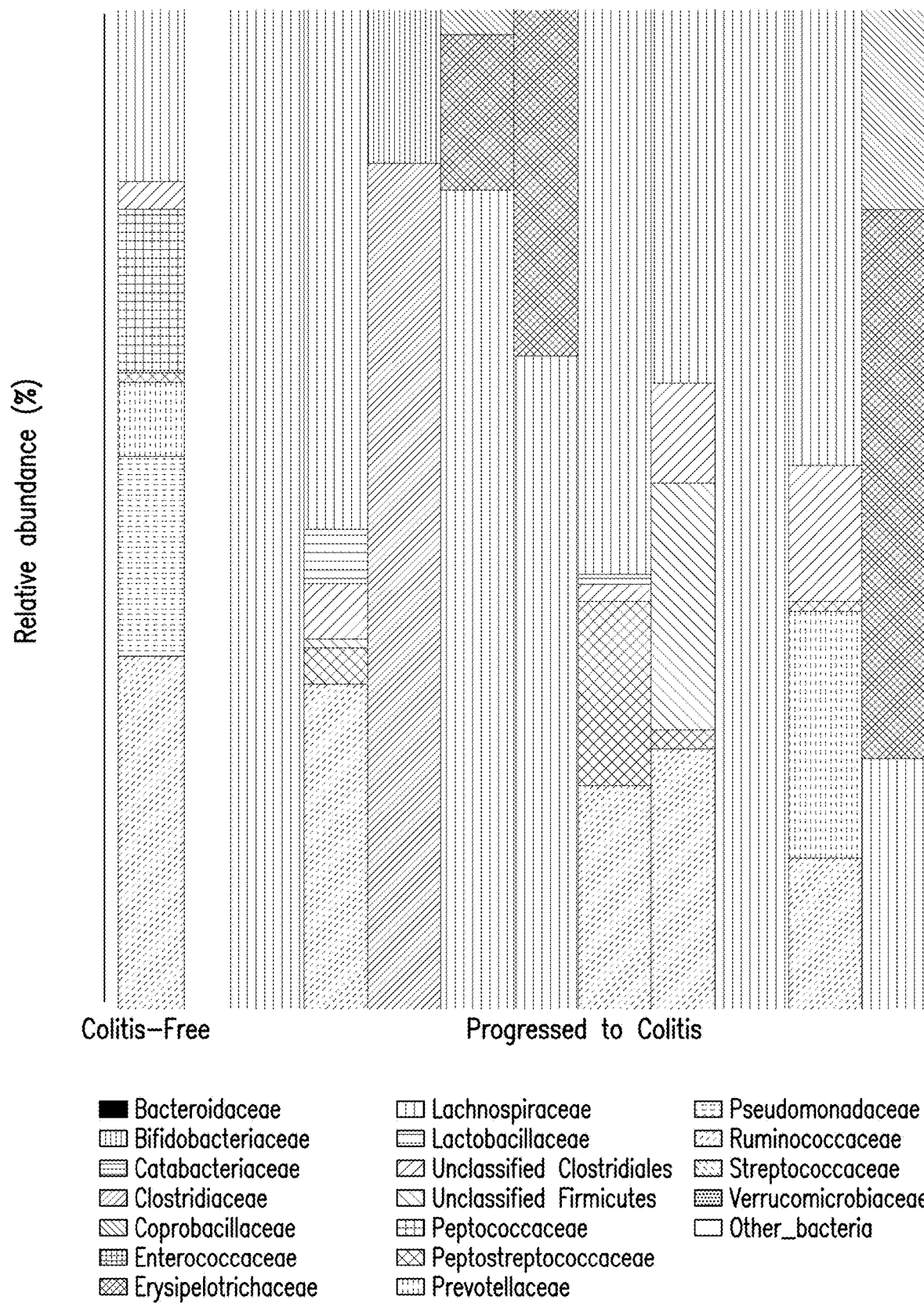
Figure 3H:
Figure 3I:
Figure 3J:
Figure 3K:
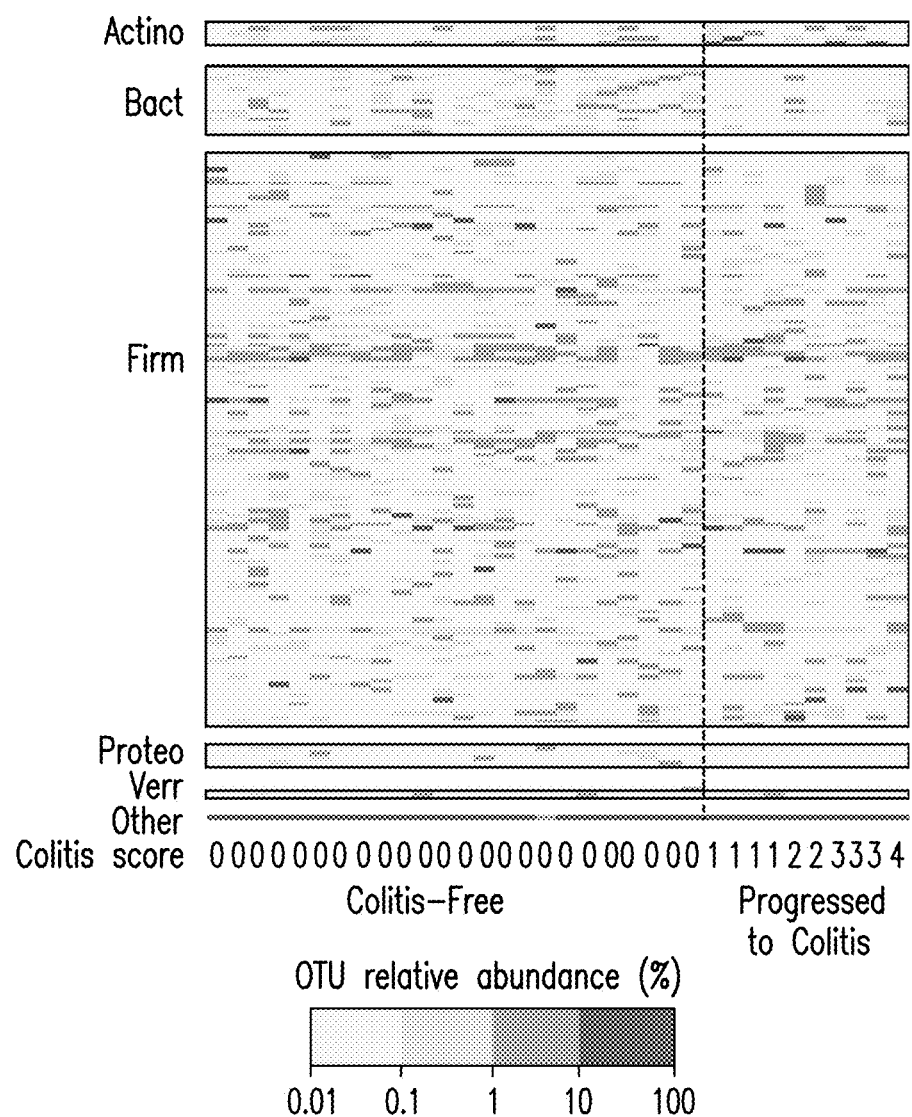

The composition of the intestinal microbiomes of patients was also assessed. OTUs with an average abundance greater than 0.01% within either patient group were classified at the family taxonomic level (FIGS. 3A-3J). The relative abundances of the 146 bacterial OTUs in C-F and PtC patients represented in a heat map. OTUs plotted were present at a mean abundance of 0.1% or greater (FIG. 3K). C-F patients harbored a greater proportion of microbes within the Bacteroidaceae family), although C-F and PtC patients shared many bacterial taxa that belong to the Firmicutes phylum.

To illustrate microbiota composition with finer resolution, relative abundances of 146 OTUs at 0.1% or greater mean abundance were plotted. Generally, broad swaths of microbiota were found at similar frequencies between C-F and PtC patient groups. However, as shown in (FIG. 3K), microbiota within the Bacteroidetes phylum are underrepresented in patients who developed new-onset, immune-mediated colitis.

To further characterize their intestinal microbiota, the fecal samples from the subjects were submitted for bacterial microbiota profiling using 16S rRNA sequencing on the Illumina MiSeq platform. To examine the intestinal microbiota structure between patient groups, relative frequencies were plotted of bacterial phylotypes at the taxonomic level of family for each patient. 16s sequencing reads were clustered into OTUs by 97% sequencing homology (FIG. 4A). Relative abundances of OTUs that met our defined threshold (of an average abundance greater than 0.01% in either patient group) were plotted by phylum. Bar plots were constructed only for those patients whose samples were subjected to shotgun metagenomic sequencing. Relative abundances of shotgun metagenomic sequencing reads were calculated using MetaPhlAn and plotted by phylum (FIG. 4B). The taxonomic classifications used, based on 16S sequencing data, were similar to those found when applying MetaPhlAn to shotgun metagenomic sequencing data on a subset of this patient cohort, although the proportions of some bacterial phyla vary between the two methods.

Figure 5A:
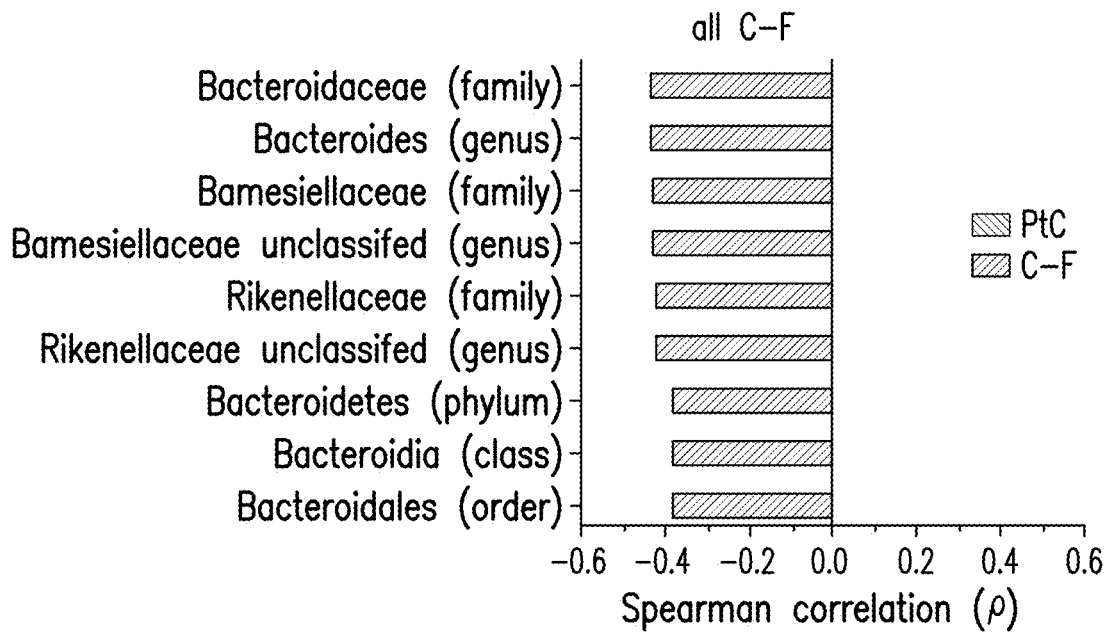
Figure 5B:
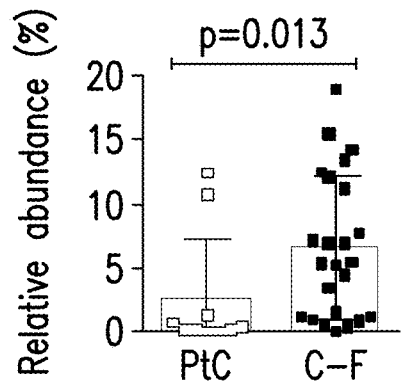
Figure 5C:
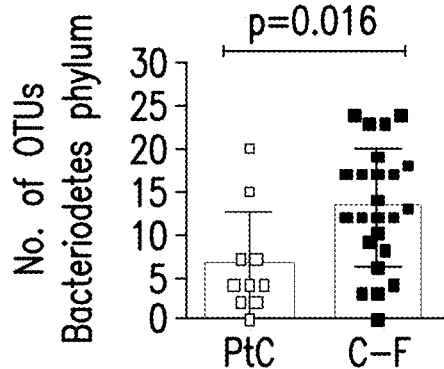
Figure 5D:
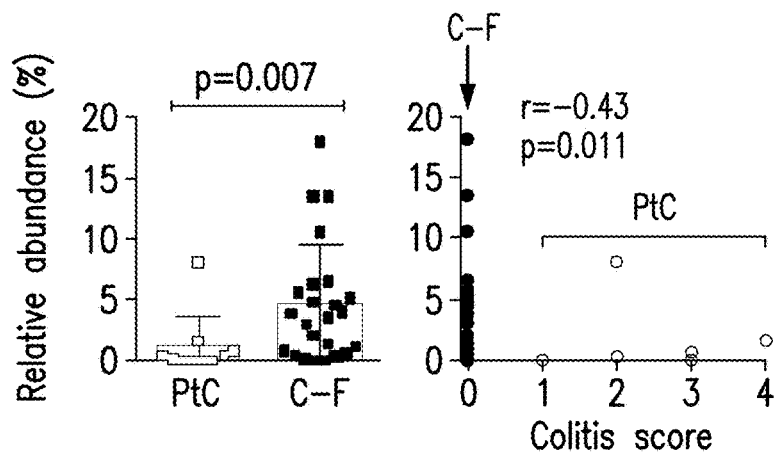
Figure 5E:
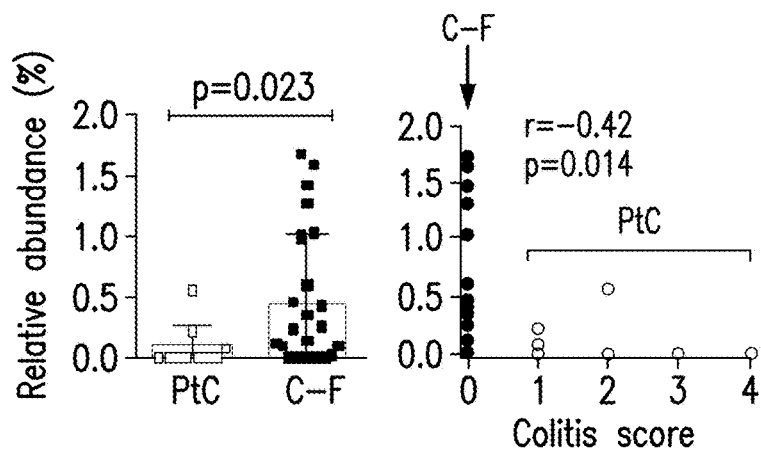
Figure 5F:
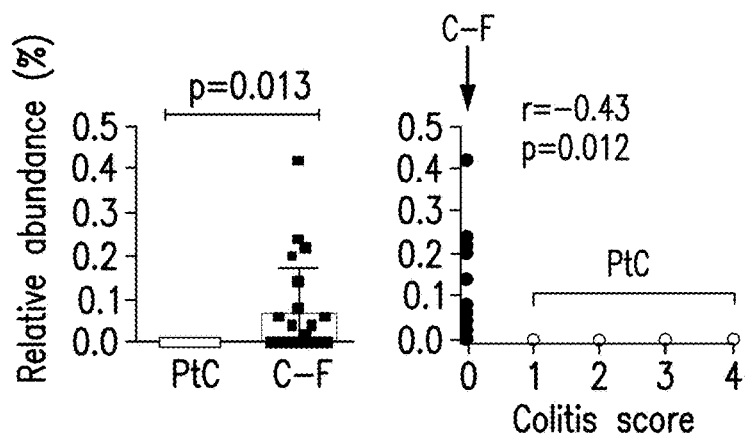

6.2(c) Members of Bacteroidetes Phylum are Associated with Resistance to Development of CTLA-4 Blockade Associated Colitis OTUs with an average abundance greater than 0.01% within either patient group were binned at different levels of taxonomic classification (phylum, class, order, family, genus). The correlation of bacterial phylotypes to CTCAE-based colitis score was compared by Spearman analysis (FIG. 5A). According to this analysis, microbiota within the Bacteroidetes phylum are more prevalent in C-F patient samples, which was demonstrated by analysis of the relative abundances of bacterial species grouped at different taxonomic levels.

Relative abundance of the phylum Bacteriodetes in PtC and C-F patients was also assessed using the Mann-Whitney test ($p<0.05$) (FIG. 5B). c) The number of OTUs assigned to the Bacteroidetes phylum in each patient group. Relative abundances of the families d) Bacteroidaceae, e) Rikenellaceae, f) Barnesiellaceae within the Bacteroidetes phylum in PtC and C-F patients The relative abundance of species classified as Bacteroidetes, as well as the number of OTUs assigned to the phylum, were significantly higher in C-F patients (Mann-Whitney test, $p<0.05$) (FIG. 3B and FIG. 3C). Within the Bacteroidetes phylum, the prevalence of Bacteroidaceae (FIG. 3D), Rikenellaceae (FIG. 3E), and Barnesiellaceae (FIG. 3F) was significantly correlated with resistance to Ipilimumab-associated colitis (Mann-Whitney test, $p<0.01$, $p<0.05$, $p<0.05$, respectively).

To assess the relationship between specific bacterial members of the intestinal microbiota and development of CTLA-4 blockade-associated colitis, subjects were first stratified by the severity of inflammation. Second, a Spearman rank correlation test was performed on the relative abundances of bacterial species grouped at different taxonomic levels. While the composition of the intestinal microbiota may vary over the lifetime of an individual, there was no association between the age of a subject and the abundance of Bacteroidetes (FIG. 6).

6.2(d) Bacterial Genetic Modules Involved in Polyamine Transport and Vitamin B Synthesis are Associated with Resistance to Colitis To evaluate the genetic pathways that may play a role in the development of immune-mediated colitis, shotgun metagenomic sequencing was performed on the 10 PtC and 12 C-F patient fecal samples. Sequencing reads were processed using HUMAnN and assigned to KEGG (Kyoto Encyclopedia of Genes and Genomes) modules. An univariate test was then conducted for associations between colitis status and the 102 microbial modules using linear discriminant analysis effect size (LEfSe).

Figure 7A:
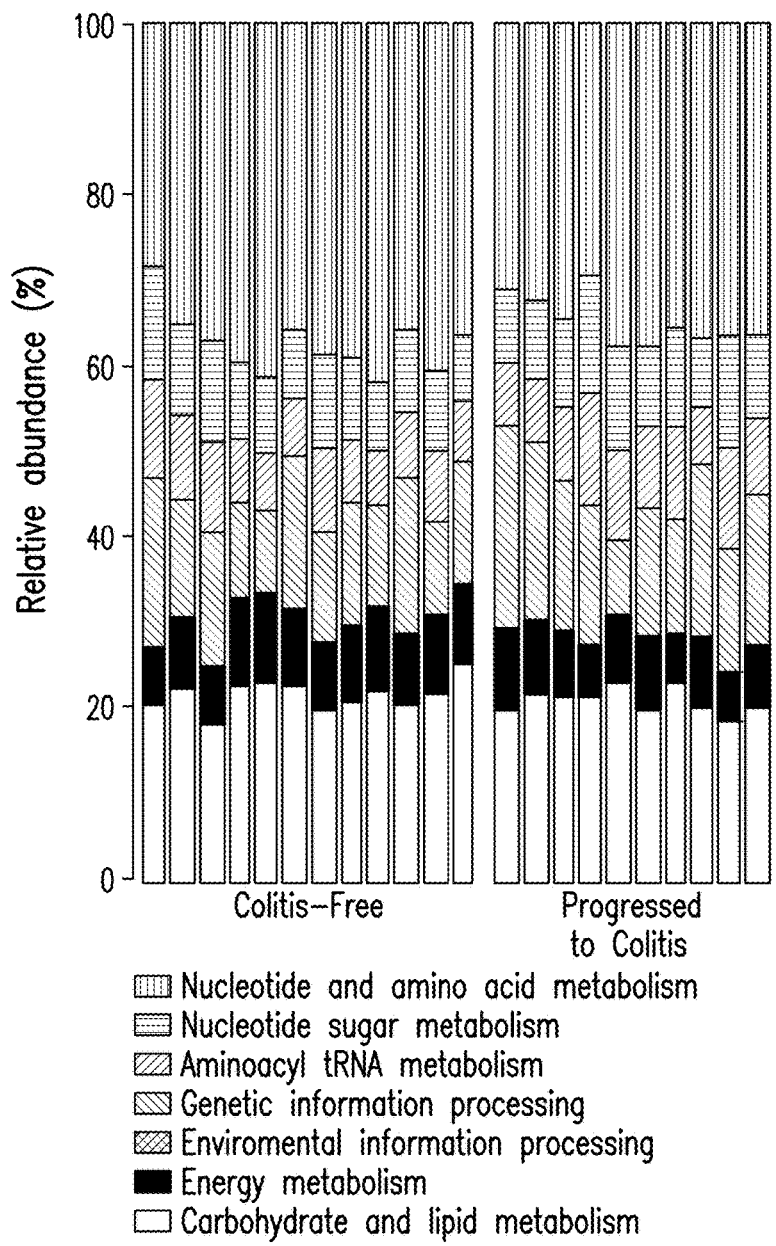

The relative abundance of 102 microbial KEGG genetic modules in C-F and PtC patients is presented in FIG. 7A. The bacterial genetic modules of the intestinal microbiota of C-F and PtC patients were broadly similar.

Figure 7B:
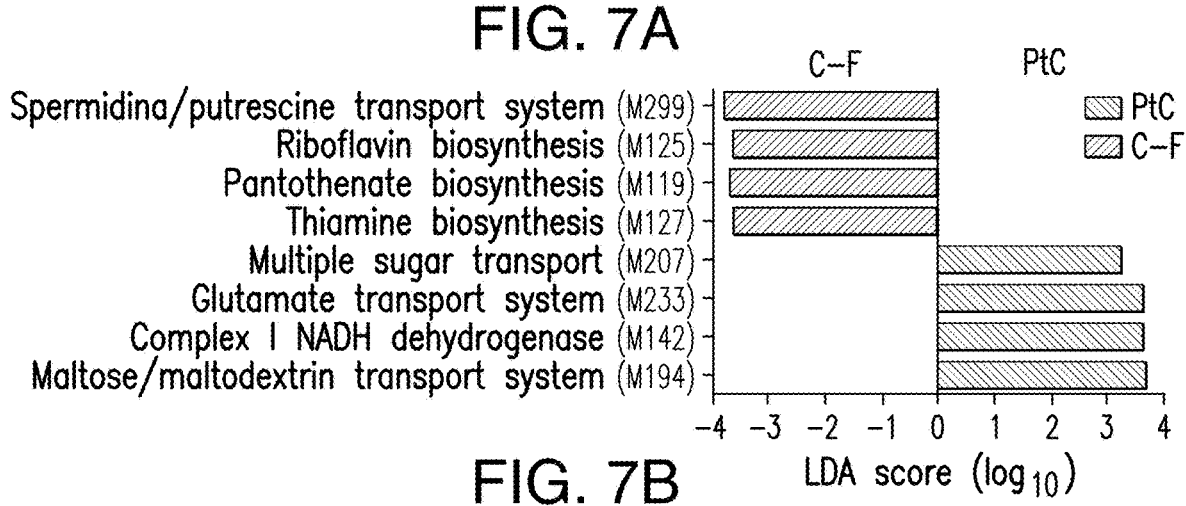

Association of genetic modules with colitis status by linear discriminant analysis effect size (LEfSe) analysis was also determined (FIG. 7B). The spermidine/putrescine polyamine transport system and three modules involved in the biosynthesis of B vitamins (riboflavin (B2), pantothenate (B5) and thiamine (B1)) were more abundant in C-F patients.

Figure 7C:
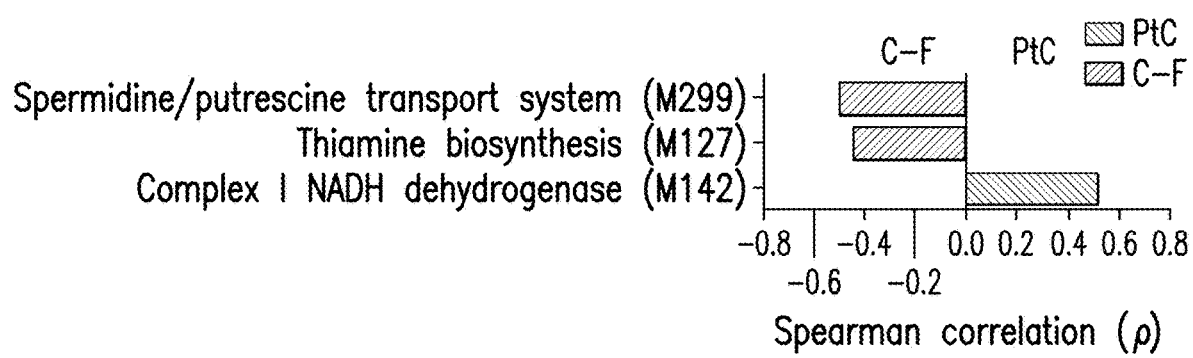

Correlation of genetic modules to colitis score by Spearman analysis was also plotted (FIG. 7C). After stratifying samples by colitis status, Spearman analysis identified the polyamine transport system and thiamine (B1) modules as correlated with resistance to the development of colitis.

Figure 7D:
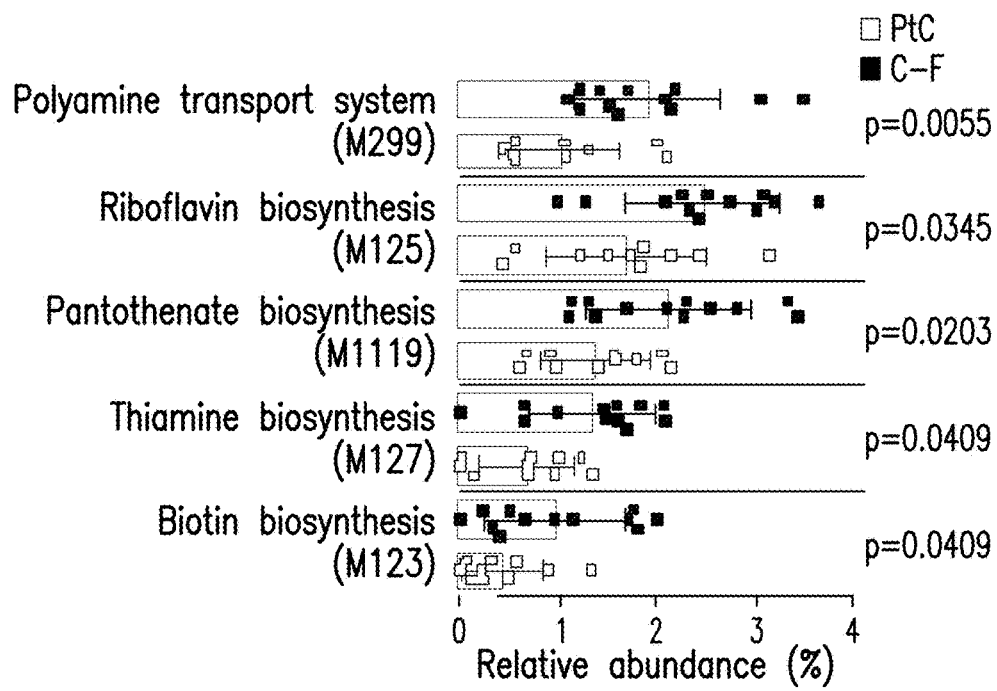

The relative abundances of the aforementioned pathways are significantly enriched in C-F patient samples (Mann-Whitney test, $p<0.05$ for all modules) (FIG. 7D). In addition, an additional module involved in the biosynthesis of the biotin (vitamin B7) was found in greater abundance in C-F patients (Mann-Whitney test, $p<0.05$) (FIG. 7D).

6.2(e) Colitis Subjects can be Identified Using Bacterial Genetic Modules

The predictive accuracy of bacterial genetic modules in identifying patients who develop checkpoint blockade therapy associated colitis was also assessed using regression analysis. For this regression analysis, the four bacterial genetic modules selected were associated with resistance to colitis as identified in the Spearman and LEfSe analyses. The four bacterial genetic modules are the polyamine transport system module and modules involved in the biosynthesis of vitamins riboflavin (B2), pantothenate (B5) and thiamine (B1).

Figure 8A:
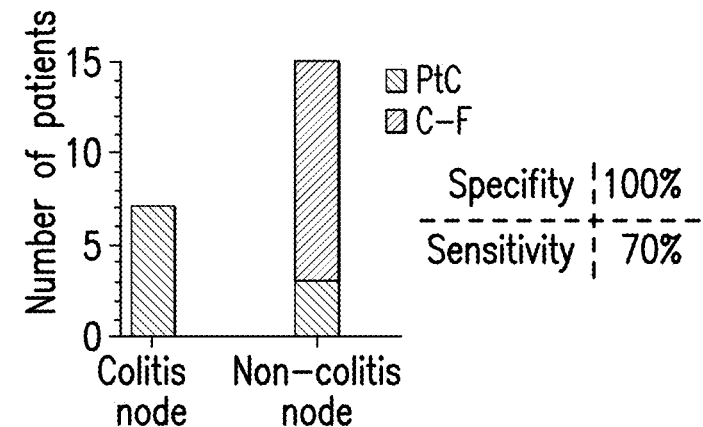

The recursive partitioning algorithm was utilized to construct a classification tree with 102 bacterial genetic modules, based on the abundance of the polyamine transport module (FIG. 8A). The samples were successfully classified as from either PtC or C-F patients using the relative abundance of polyamine transport system module alone. A sensitivity of 70% and specificity of 100% was achieved in analysis of the PtC subjects, based on 7 samples appropriately identified, and 3 samples misclassified as C-F.

The recursive partitioning algorithm was also successfully used to estimate colitis status of patient samples based on polyamine transport system abundance alone. Samples with a module abundance of 1% or greater were classified as Colitis-Free by this algorithm. (FIG. 9).

Figure 8B:
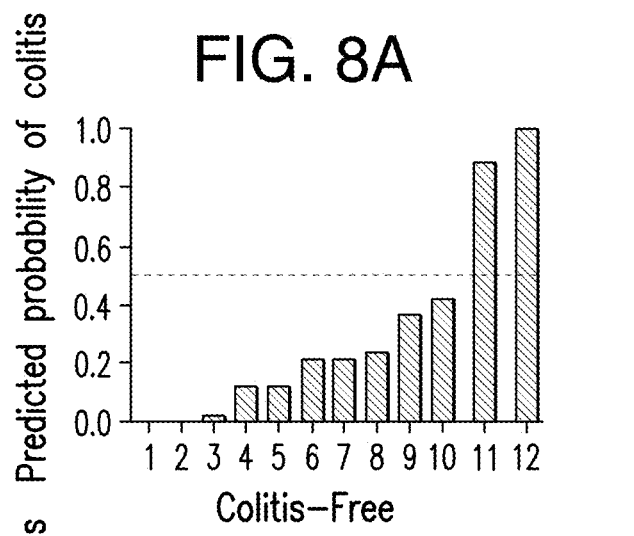
Figure 8B:
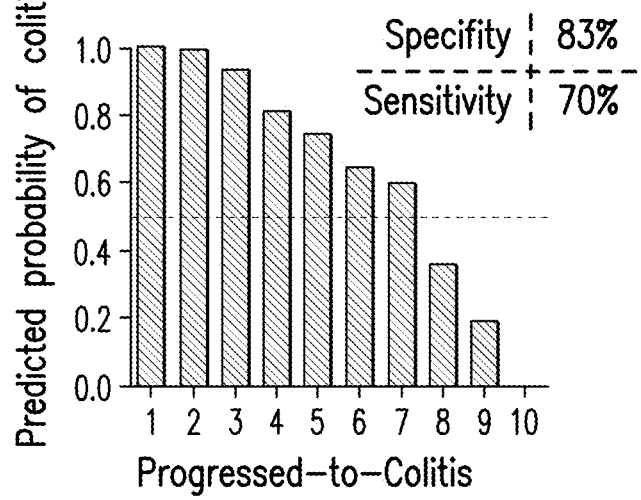

A leave-one-out cross-validation of the probit regression analysis was able to predict the probability of colitis using four bacterial genetic modules associated with colitis resistance: polyamine transport system, thiamine biosynthesis, riboflavin biosynthesis, and pantothenate biosynthesis (FIG. 8B). Colitis status was correctly predicted for 10 out of 12 C-F patients and 7 out of 10 PtC patients, at a probability threshold of 50%. This model results in a sensitivity of 70% and specificity of 83%.

Figure 8C:
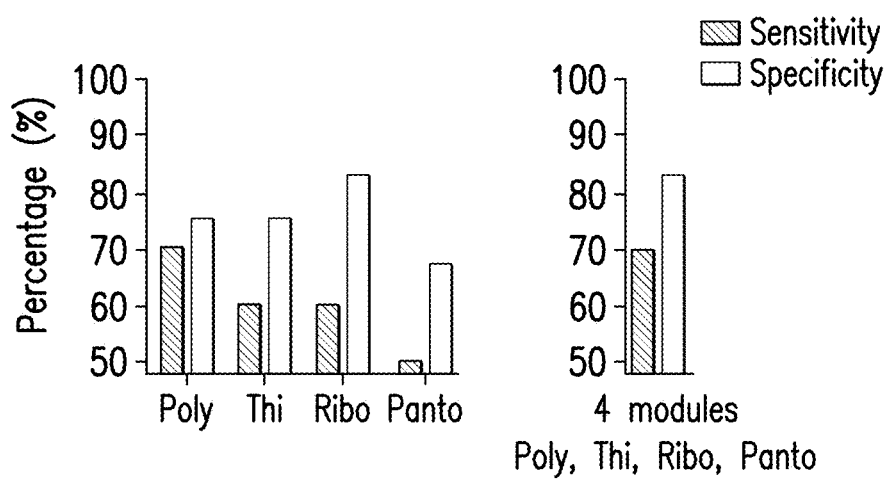

In FIG. 8C, the sensitivity and specificity of each separate bacterial genetic module to predict patients' colitis status by their fecal microbial samples was determined using a probability threshold of 50%, as compared to the four-module model presented in FIG. 8B. As shown in FIG. 8C, the four bacterial genetic modules were more predictive in combination as compared to any individual module.

Figure 8D:
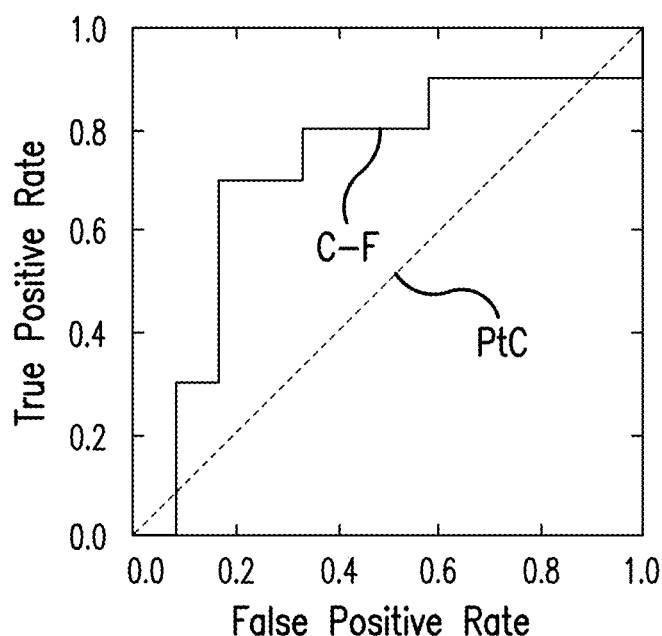

As shown in FIG. 8D, an ROC curve of the four-module model predicting colitis risk was created by calculating the True Positive Rate and False Positive Rate for 10,000 thresholds of the predicted probability of colitis between 0 and 1. True Positive Rate represents the test sensitivity, calculated by: True Positives/(True Positives+False Negatives). False Positive Rate, which is given by 1 minus the test specificity, is calculated by: False Positives/(False Positives+True Negatives).

In combination, the four-module analysis predicts colitis risk with good accuracy. Based on the analytical models described herein, the four modules selected serve as biomarkers for patients at high risk of developing CTLA-4 blockade associated colitis because such analytical models identify bacterial pathways that may confer resistance to colitis.

The invention claimed is:

1. A pharmaceutical composition for reducing the risk or severity of checkpoint blockade therapy-associated colitis comprising isolated bacteria or spores thereof comprising (i) a member of the Bacteroidaceae family and (ii) a member of the Barnesiellaceae family, and further comprising:
   (a) a biocompatible pharmaceutical carrier selected from saline, buffered saline, dextrose, glycerol and polyethylene glycol;
   (b) an additional therapeutic agent selected from a probiotic, a prebiotic, a postbiotic and an antibiotic;
   (c) a solubilizer; or
   (d) a preservative,
   wherein the pharmaceutical composition is formulated for oral, nasogastric or rectal administration, and
   wherein the isolated bacteria or spores thereof are present in a therapeutically effective amount that reduces the risk or severity of checkpoint blockade therapy-associated colitis in a subject administered the pharmaceutical composition.

2. The pharmaceutical composition of claim 1, further comprising an isolated bacteria or spores thereof of a member of the Rikenellaceae family.

3. The pharmaceutical composition of claim 1, wherein one or more of the isolated bacteria is a recombinant cell.

4. The pharmaceutical composition of claim 1, wherein the pharmaceutical composition is a liquid, suspension, dried powder, tablet, capsule or food product.

5. The pharmaceutical composition of claim 1, wherein the pharmaceutical composition further comprises a probiotic bacteria, probiotic yeast, or a combination thereof; a prebiotic; a postbiotic; an antibiotic; or combination thereof.

6. The pharmaceutical composition of claim 1, wherein one or more of the isolated bacteria or spores thereof are lyophilized.

* * * * *

```
                        SEQUENCE LISTING

<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other

<400> SEQUENCE: 1
nnnnnnnnnn nnnnnnnnnn aytgggydta aagng                              35

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(20)
<223> OTHER INFORMATION: a, c, t, g, unknown or other

<400> SEQUENCE: 2
nnnnnnnnnn nnnnnnnnnn ccgtcaatty htttragt                           38
```